(12) United States Patent
Reidt et al.

(10) Patent No.: US 8,561,845 B2
(45) Date of Patent: Oct. 22, 2013

(54) CAPSULE FOR TWO-COMPONENT MATERIALS

(75) Inventors: Dean K Reidt, Cottage Grove, MN (US); Darin J Meyertholen, Woodbury, MN (US); Bruce R Broyles, Oakdale, MN (US); Robert Lee, Lake Elmo, MN (US); Robert M Biegler, Woodbury, MN (US); Arno Hohmann, Munich (DE); Marc Peuker, Schondorf (DE); Michael Knee, Peissenberg (DE)

(73) Assignees: 3M Innovative Properties Company, St. Paul, MN (US); 3M ESPE AG, Seefeld (DE)

( * ) Notice: Subject to any disclaimer, the term of this patent is extended or adjusted under 35 U.S.C. 154(b) by 0 days.

(21) Appl. No.: 12/976,238

(22) Filed: Dec. 22, 2010

(65) Prior Publication Data

US 2011/0084094 A1  Apr. 14, 2011

Related U.S. Application Data

(62) Division of application No. 10/568,247, filed as application No. PCT/EP2004/007178 on Jul. 1, 2004, now Pat. No. 7,882,983.

(30) Foreign Application Priority Data

Aug. 14, 2003 (DE) .................................. 103 37 790
Jun. 4, 2004 (EP) ..................................... 04013277

(51) Int. Cl.
*B67D 7/70* (2010.01)

(52) U.S. Cl.
USPC ...................................... 222/137; 222/145.5

(58) Field of Classification Search
USPC ............ 222/137, 146.6, 146.5, 94, 129, 136, 222/135, 142.9, 145.7, 145.8, 566, 567, 222/145.6, 145.5
See application file for complete search history.

(56) References Cited

U.S. PATENT DOCUMENTS

| | | | |
|---|---|---|---|
| 2,032,776 A | | 3/1936 | Ness |
| 2,168,686 A | * | 8/1939 | Saffir ............................ 604/415 |
| 3,089,626 A | | 5/1963 | Kubiliunas |
| 3,144,966 A | * | 8/1964 | Cook ............................. 222/136 |
| 3,251,516 A | | 5/1966 | Thomas |
| 3,323,682 A | | 6/1967 | Creighton |
| 3,767,085 A | * | 10/1973 | Cannon et al. .................. 222/82 |
| 3,863,818 A | | 2/1975 | Hazard |
| 3,952,920 A | * | 4/1976 | Bergman ....................... 222/137 |
| 4,121,739 A | | 10/1978 | Devaney et al. |

(Continued)

FOREIGN PATENT DOCUMENTS

| | | |
|---|---|---|
| CH | 669 164 | 1/1989 |
| CN | 2397066 | 9/2000 |

(Continued)

*Primary Examiner* — Lien Ngo

(57) ABSTRACT

Capsule (10) for two or more components of a material which are to be mixed together, comprising a cartridge (11) comprising an outlet (12), a first component chamber (13) for containing a first component, and a second component chamber (14) for containing a second component, the two chambers (13, 14) opening into the outlet (12); and a piston (15) which at least with its front end sits in the cartridge (11), lies with its rear end outside the component chambers (13, 14) and, when it is pushed forwards, presses the two components out of their component chambers (13, 14).

16 Claims, 25 Drawing Sheets

(56) References Cited

U.S. PATENT DOCUMENTS

| | | | |
|---|---|---|---|
| 4,471,888 A | 9/1984 | Herb et al. | |
| 4,538,920 A | 9/1985 | Drake | |
| 4,674,661 A * | 6/1987 | Herold | 222/386 |
| 4,687,663 A | 8/1987 | Schaeffer | |
| 4,735,509 A | 4/1988 | Rausch | |
| 4,801,008 A | 1/1989 | Rich | |
| 4,823,946 A | 4/1989 | Stoeffler | |
| 4,995,540 A | 2/1991 | Colin et al. | |
| 5,033,650 A | 7/1991 | Colin et al. | |
| 5,065,906 A | 11/1991 | Maeder | |
| RE33,801 E | 1/1992 | Green | |
| 5,082,147 A | 1/1992 | Jacobs | |
| 5,127,548 A | 7/1992 | Brunet et al. | |
| 5,137,181 A | 8/1992 | Keller | |
| 5,152,432 A | 10/1992 | De Laforcade | |
| 5,242,082 A | 9/1993 | Giannuzzi | |
| 5,249,709 A | 10/1993 | Duckworth et al. | |
| 5,333,760 A | 8/1994 | Simmen | |
| 5,370,221 A | 12/1994 | Magnusson et al. | |
| 5,535,922 A | 7/1996 | Maziarz | |
| 5,647,510 A | 7/1997 | Keller | |
| 5,743,436 A | 4/1998 | Wilcox et al. | |
| 5,897,028 A | 4/1999 | Sauer | |
| 6,047,861 A | 4/2000 | Vidal et al. | |
| 6,048,201 A | 4/2000 | Zwingenberger | |
| 6,065,643 A | 5/2000 | Harvey et al. | |
| 6,296,149 B1 | 10/2001 | Long | |
| 6,352,177 B1 | 3/2002 | Bublewitz et al. | |
| 6,375,460 B1 | 4/2002 | Plaumann | |
| 6,386,872 B1 | 5/2002 | Mukasa et al. | |
| 6,409,972 B1 * | 6/2002 | Chan | 422/131 |
| 6,454,129 B1 | 9/2002 | Green | |
| 6,464,112 B2 | 10/2002 | Summons et al. | |
| 6,547,101 B1 | 4/2003 | Sogaro | |
| 6,681,957 B1 | 1/2004 | Green | |
| 6,843,652 B2 | 1/2005 | Xie et al. | |
| 7,367,475 B2 * | 5/2008 | Horth et al. | 222/145.6 |
| 7,882,983 B2 | 2/2011 | Reidt | |
| 2002/0023892 A1 | 2/2002 | Savitz et al. | |
| 2003/0111490 A1 | 6/2003 | Pierson | |
| 2003/0147688 A1 | 8/2003 | Hathaway | |
| 2004/0104249 A1 | 6/2004 | Horth et al. | |
| 2004/0152041 A1 | 8/2004 | Metzbower | |
| 2005/0130099 A1 | 6/2005 | Besek et al. | |
| 2006/0273109 A1 | 12/2006 | Keller | |

FOREIGN PATENT DOCUMENTS

| | | |
|---|---|---|
| DE | 2 219 009 | 10/1973 |
| DE | 39 13 409 | 10/1990 |
| DE | 39 134 09 | 10/1990 |
| DE | 90 16 568 | 5/1992 |
| DE | 92 06 892 | 1/1993 |
| DE | 197 08 548 | 9/1998 |
| DE | 696 17 260 | 7/2002 |
| DE | 101 33 075 | 1/2003 |
| DE | 101 51 104 | 4/2003 |
| EP | 00 931 85 | 11/1983 |
| EP | 0 157 121 | 10/1985 |
| EP | 0 249 701 | 12/1987 |
| EP | 0 783 872 | 7/1997 |
| EP | 0 831 034 | 3/1998 |
| EP | 1 430 959 | 6/2004 |
| EP | 1 544 123 | 6/2005 |
| FR | 1 493 380 | 8/1967 |
| JP | S62-65969 | 3/1987 |
| JP | S61-99566 | 7/1994 |
| JP | 2002-145360 | 5/2002 |
| WO | WO 94/14698 | 7/1994 |
| WO | WO 95/22941 | 8/1995 |
| WO | WO 96/15705 | 5/1996 |
| WO | WO 97/21394 | 6/1997 |
| WO | WO 01/44065 | 6/2001 |
| WO | WO 02/094683 | 11/2002 |
| WO | WO 2005/016783 | 2/2005 |

* cited by examiner

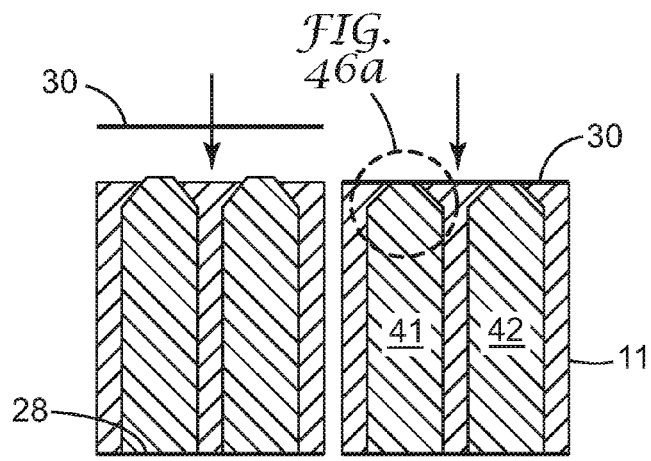
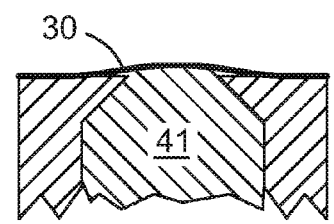
FIG. 46   FIG. 46a
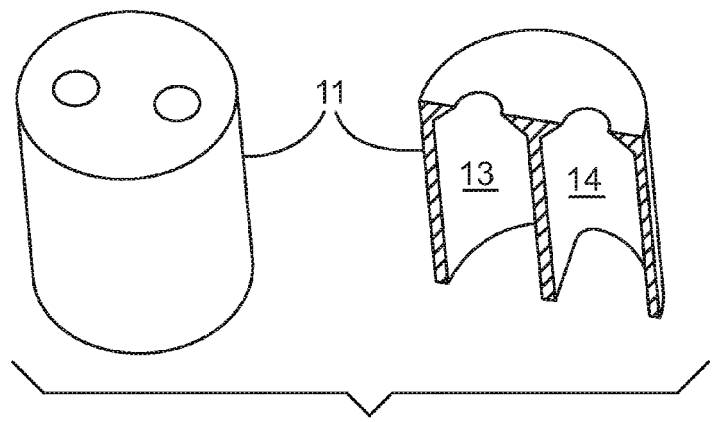
FIG. 47
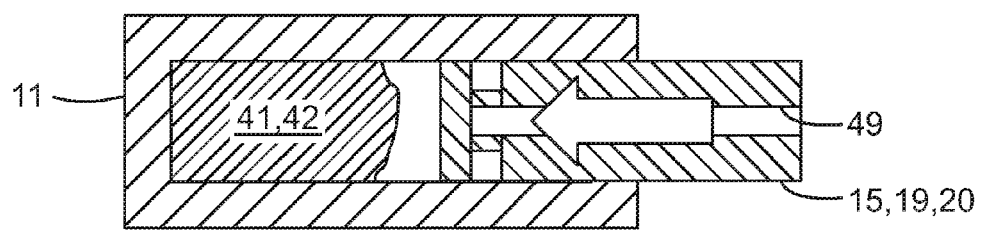
FIG. 48

CAPSULE FOR TWO-COMPONENT MATERIALS

CROSS-REFERENCE TO RELATED APPLICATIONS

The present application is a divisional of U.S. patent application Ser. No. 10/568,247, filed Nov. 14, 2006, now U.S. Pat. No. 7,882,983 which is a U.S. 371 National Stage Patent Application of PCT/EP2004/007178, filed Jul. 1, 2004, which claims priority from German Patent No. DE 103 37 790.5, filed Aug. 14, 2003, and from European Patent No. EP 04 013 277.1, filed Jun. 4, 2004.

BACKGROUND OF THE INVENTION

1. Field of the Invention

The invention relates to a capsule for two or more components of a material which are to be mixed together. The material can be a dental material, for example an impression material, a temporary restoration material or a filler material.

2. Background

In the dental sector, that is to say the sector involving dentists and dental technicians, various capsules are known for intraoral administration of materials consisting of one component or of two or more components which are to be mixed together. There are so-called "compules", liquid/powder capsules, and paste/paste capsules.

The compule is a capsule having a cannula, a single chamber containing a one-component material and opening at the front into the cannula, and a piston which sits in the chamber at the rear. Such compules can contain, for example, the universal filler material Filtek™ Supreme and the universal composite Filtek™ Z250 available from 3M ESPE. For use, they have to be inserted into an applicator 62 (shown in FIG. 69) which, for example, is available from 3M ESPE as Capsule dispenser under article number 5706 SD or from Centrix™. These known applicators 62 each have a body with a handgrip, a holder for receiving the compule in a removable manner, a plunger, and a drive mechanism for the plunger. When the capsule sits in the holder and the drive mechanism is actuated by closing the hand, said drive mechanism then pushes the plunger into the chamber from the rear, so that said plunger initially bears on the piston and pushes it farther forwards. By means of the advance movement of the piston, the material is dispensed from the chamber through the cannula. Such compule applicators 62 are very widely available on the market.

The liquid/powder capsules contain a liquid component and a powder component which have to be kept separate from one another until the time of use. Such liquid/powder capsules are, for example, available under the names Aplicap™ and Maxicap™ from 3M ESPE. These capsules contain, for example, the two components, to be mixed together, of filler materials such as, for example, the glass ionomer filler material Ketac™ Molar, or the light-cured glass ionomer filler material Photac™ Fil Quick, or the silver-reinforced glass ionomer filler material Ketac™ Silver Molar, or luting cements such as, for example, the self-adhesive universal composite luting cement RelyX™ Unicem or the adhesive composite luting cement Compolute™ or the glass ionomer luting cement Ketac™ Cem. These known capsules have a cannula, a large mixing chamber which contains the powder and opens at the front into the cannula, a piston which sits at the rear in the mixing chamber, and a foil pouch which contains the liquid and covers a hole in the shell or outer wall of the chamber. To use it, the capsule is first activated by applying pressure in a suitable way to the foil pouch, so that the latter tears over the hole and the liquid is forced into the mixing chamber. The mixing chamber is larger than the joint volume of the two components, so that these can be mixed together by vigorous agitation, for example using the capsule mixer devices RotoMix™ or CapMix™ from 3M ESPE. They then have to be inserted into a suitable applicator 62, which for example is obtainable under the name Aplicap™ Applier (shown in FIG. 70) or Maxicap™ Applier from 3M ESPE. These known applicators 62 each have a body with a handgrip, a holder for receiving the capsule in a removable manner, a plunger 63, and a drive mechanism for the plunger 63. When the capsule sits in the holder and the drive mechanism is actuated by closing the hand, said drive mechanism then pushes the plunger 63 into the mixing chamber from the rear, so that said plunger 63 initially bears on the piston and pushes it farther forwards. By means of the advance movement of the piston, the material is dispensed from the mixing chamber through the cannula. Such applicators 62 for liquid/powder capsules are likewise widely available on the market.

The paste/paste capsules contain two pasty components which have to be kept separate from one another until the time of use. Such a paste/paste capsule is known from WO 97/21394, which additionally discloses an applicator for this capsule. This known capsule has a cannula, a static mixer, which sits in the cannula, two cylindrical chambers lying alongside one another and opening at the front into the cannula, and two cylindrical pistons which sit displaceably in the rear of the chambers. The known applicator has a body with a handgrip, a holder for receiving the capsule in a removable manner, two elongate plungers lying alongside one another, and a drive mechanism for the two plungers which, when the capsule sits in the holder, advances these into the two chambers from the rear. The chambers contain the two pasty components which, upon actuation of the applicator drive mechanism, are pressed forwards out of the chambers and into the cannula by the two pistons which are pushed farther into the chambers by the two plungers. Upon further flow through the cannula, the two component strands are mixed together by means of the mixer and finally dispensed as a ready-mixed material from the front of the cannula.

The paste/paste capsule known from WO 97/21394 cannot be used with the known compule applicators 62 described above, nor with the above-described known applicators 62 for liquid/powder capsules, both of which forms are widely available on the market, because these each have only a single plunger 63, while the known paste/paste capsule has two pistons.

SUMMARY OF THE INVENTION

The Invention provides the advantage that the capsule according to the present invention can be used with an applicator having a single plunger which is advanced when the applicator is actuated. Above all, the capsule according to the present invention can be designed without great expense in such a way that it matches the compule applicators already available on the market or the applicators for liquid/powder capsules. In this way it is possible to avoid the expense of producing a new applicator and bringing it onto the market.

A further advantage of the invention results from the fact that the capsule interface is adapted to be used with existing applicators having a single plunger. In this way, future developments of paste materials and appropriate capsules are not limited to two-component systems and are independent from standard mixing ratios as all paste material specific details are included in the capsule itself. Thus a modification of the applicator would not be necessary.

The proposed solutions of the invention all relate to the packaging of pastes, which are to be understood as including liquid to pasty substances, preferably for dental applications.

In a first aspect, the invention relates to a capsule for two or more components of a material which are to be mixed together, comprising:
- a cartridge comprising an outlet, a first component chamber for containing a first component, and a second component chamber for containing a second component, the two chambers opening into the outlet; and
- a piston which at least with its front end sits in the cartridge, lies with its rear end outside the component chambers and, when it is pushed forwards, presses the two components out of their component chambers.

In a second aspect, the invention relates to a capsule for two or more components of a material which are to be mixed together, comprising:
- a cartridge comprising an outlet, a first component chamber for containing a first component, and a second component chamber for containing a second component, the two component chambers opening into the outlet;
- a first piston which at least with its front end sits in the first component chamber, and a second piston which at least with its front end sits in the second component chamber, which two pistons lie with their rear ends outside the component chambers and, when they are pushed forwards, press the two components out of their component chambers.

Since the two pistons lie with their rear ends outside the chambers, one plunger can bear on both rear ends and push both pistons jointly farther forwards into their chambers.

In a third aspect, the invention relates to a capsule for two or more components of a material which are to be mixed together, comprising:
- a cartridge comprising an outlet, a first component chamber for containing a first component, and a second component chamber for containing a second component, the two component chambers opening into the outlet; and
- each of the two component chambers being at least partially delimited by a foil.

Since each of the two chambers is at least partially delimited by a foil, one plunger can bear against the foil which, upon further advance of the plunger, is applied against the chamber wall, so that the components enclosed under the foil are squeezed out of the chambers from the front in the same way as from a tube.

In a fourth aspect, the invention relates to a capsule for two or more components of a material which are to be mixed together, comprising:
- a cartridge comprising a first component chamber for containing a first component and a second component chamber for containing a second component;
- a housing comprising an outlet and a cartridge chamber for holding the cartridge, the cartridge chamber being connected to the outlet;
- a first piston for movement within the first component chamber, and a second piston for movement within the second component chamber.

In a fifth aspect, the invention relates to a capsule for two or more components of a material which are to be mixed together, comprising:
- a first cartridge comprising a first component chamber for containing a first component, and a second cartridge comprising a second component chamber for containing a second component;
- a housing comprising an outlet and a cartridge chamber for holding the cartridges, the cartridge chamber being connected to the outlet;
- a first piston for movement within the first component chamber, and a second piston for movement within the second component chamber.

In a sixth aspect, the invention relates to a capsule for two or more components of a material which are to be mixed together, comprising:
- a first cartridge comprising a first component chamber for containing a first component, and a second cartridge comprising a second component chamber for containing a second component;
- a housing comprising an outlet, a first cartridge chamber for holding the first cartridge, and a second cartridge chamber for holding the second cartridge, the first and second cartridge chambers being connected to the outlet;
- a first piston for movement within the first component chamber, and a second piston for movement within the second component chamber.

Preferred features and embodiments of the invention are described in the claims.

It may be provided that each of the two component chambers is separated from the rest of the interior of the cartridge by a flexible partition wall.

It may be provided that a common partition wall separates the two chambers from one another.

It may be provided that the partition wall is secured or fixed at least with part of its edge on the cartridge, preferably by adhesive bonding or welding, or in one piece therewith.

It may be provided that the partition wall is secured or fixed with the rear part of its edge on the front end of the piston, preferably by adhesive bonding or welding, or in one piece therewith.

It may be provided that:
- the cartridge is divided in the axial direction into two shells for receiving the two components; and
- each of the two shells is closed off by a foil.

It may be provided that the two shells are connected to one another, preferably by adhesive bonding or welding.

It may be provided that the two shells are connected to one another in a foldable manner at two adjoining edges. The two other edges can have corresponding locking means.

It may be provided that the two shells are closed off by a common foil and are also connected to one another in a foldable manner.

It may be provided that each of the two chambers is separated from the rest of the interior of the cartridge by a rigid partition wall.

It may be provided that a common partition wall separates the two chambers from one another.

It may be provided that the partition wall is secured or fixed at least with part of its edge on the cartridge, preferably by adhesive bonding or welding, or in one piece therewith.

It may be provided that the rear end of the partition wall bears laterally on the allocated piston.

It may be provided that the two pistons are connected fixedly to one another at their rear ends, preferably by adhesive bonding or welding, or in one piece therewith.

It may be provided that:
- each chamber is closed off at its rear end by a sealing foil, preferably by adhesive bonding or welding or hot-sealing; and
- each piston lies with its front end behind the outer surface of the allocated sealing foil.

It may be provided that the sealing foil and the allocated piston are configured in such a way that the piston, when advanced into the chamber, pierces the sealing foil about its entire circumference.

It may be provided that the sealing foil and the allocated piston are configured in such a way that the piston, when advanced into the chamber, pierces the sealing foil only in the area of the cartridge wall. When advanced farther, the piston applies the sealing foil to the partition wall.

It may be provided that the sealing foil has a predetermined break point in the area of the cartridge wall and/or the allocated piston has a piercing tip or piercing edge in the area of the cartridge wall.

It may be provided that:
the cartridge has an interior with a stepped diameter, the front area being narrower than the rear area;
the component chambers are arranged in the front area; and
the sealing foil is secured or fixed on the circumferential step surface, preferably by adhesive bonding or welding or hot-sealing, and closes off the rear openings of the chambers.

It may be provided that each chamber is closed off at its front end by a sealing foil, preferably by adhesive bonding or welding or hot-sealing.

In a first alternative, it may be provided that:
a first foil at least partially delimits the first component chamber and separates it from the rest of the interior of the cartridge; and
a second foil at least partially delimits the second component chamber and separates it from the rest of the interior of the cartridge.

In a second alternative, it may be provided that:
a common foil at least partially delimits each of the two component chambers and separates them from one another;
the common foil separates the first component chamber from the rest of the interior of the cartridge; and
a closure means seals the second component chamber off from the outside.

It may be provided that the closure means is a sealing foil. It may be provided that the sealing foil closes off the rear opening of the cartridge.

It may be provided that a piston sits at least with its front end in the cartridge, lies with its rear end outside the chambers and, when it is pushed forwards, presses the two components out of their chambers. It may be provided that the piston seals the second chamber/cartridge off from the outside.

It may be provided that the foil is designed as a leaf and is secured or fixed with its edge on the cartridge, preferably by adhesive bonding or welding.

It may be provided that the foil is designed as a pouch and its edge surrounds the outlet opening. The pouch can be a tube which is closed off at the rear.

It may be provided that the pouch is secured or fixed with at least part of its outer surface on the inner face of the cartridge, preferably by adhesive bonding or welding.

It may be provided that the foil is secured or fixed on the front end of the piston, preferably by adhesive bonding or welding.

It may be provided that a sealing foil closes off the rear opening of the cartridge.

It may be provided that the sealing foil is designed as a leaf, is secured or fixed with its edge on the edge of the rear opening of the cartridge, and covers the rear ends of the pistons.

It may be provided that the sealing foil is designed as a ring, preferably as a circular ring, or as the jacket surface of a truncated cone or as the jacket surface of a spherical layer, is secured or fixed with its outer edge on the edge of the rear opening of the cartridge, and is secured or fixed with its inner edge on the jacket surface and/or rear end of the piston.

It may be provided that a cannula, in which a mixer is arranged, is mounted on the outlet of the cartridge.

It may be provided that the cannula contains means to align the mixer in a defined position or anti-twist means. Preferably one or two pins arranged in the inner surface of the cannula are used which rotate the mixer into a defined position when it is fitted into the cannula.

It may be provided that the outlet of the cartridge is provided with means which are used for attachment of a cannula in which a mixer is arranged.

It may be provided that the cannula, in a first position, closes off the outlet of the cartridge and, in a second position, is connected to the outlet of the cartridge.

It may be provided that the cannula is mounted pivotably and/or displaceably on the cartridge.

It may be provided that the cannula is mounted with a press fit on the cartridge.

It may be provided that the outlet of the cartridge is closed off by a stopper. The stopper is pushed forwards out of the outlet when pressure is exerted on the components.

It may be provided that the stopper is connected fixedly to the mixer, preferably by adhesive bonding or welding, or in one piece therewith. The stopper is pushed forwards together with the mixer when pressure is exerted on the components, so that the stopper frees the outlet.

It may be provided that the centre axis of the capsule and of the cannula is curved.

It may be provided that:
the cartridge has an interior with a stepped diameter, the front area being wider than the rear area;
the chambers are arranged in the front area; and
the piston has a jacket surface matching the stepped interior and sits with its front end in the front area and with its rear end in the rear area.

It may be provided that the cartridge has a front opening which is closed off by a cap in which the cannula is mounted.

It may be provided that the capsule has means which are used for coupling the capsule to an applicator having a single plunger which is advanced when the applicator is actuated.

It may be provided that the capsule is configured in such a way that it can be coupled to an applicator having a single plunger which is advanced when the applicator is actuated.

It may be provided that the two pistons sit with their rear ends in the cartridge when the piston has not yet been advanced or has been partially or completely advanced.

In a seventh aspect, this invention relates to a method for dispensing a material consisting of two or more components which are to be mixed together, said method comprising steps in which:
a) a capsule according to the invention is produced, each component chamber containing the allocated component;
b) if necessary, a cannula in which a mixer is arranged is attached to the outlet of the cartridge;
c) an applicator is produced, having:
   a plunger which is advanced when the applicator is actuated, and
   means which are used for attaching the capsule in such a way that the plunger can be pushed into the cartridge from the rear;
d) the capsule is attached to the applicator; and
e) the applicator is actuated in such a way that the plunger is pushed forwards in the cartridge.

By means of the advance of the plunger, the components are pressed out of their chambers through the outlet and into the cannula, and the mixed material is dispensed from the cannula.

In an eighth aspect, this invention relates to a method for producing a capsule according to the invention, wherein each component chamber contains the respective component, said method comprising steps in which:
a) the cartridge is produced;
b) the pistons are produced;
c) each component chamber is filled with the respective component;
d) the front portion of each component chamber is closed;
e) a fluid sealant, preferably a hotmelt is filled through the rear opening of each component chamber onto the component already contained therein;
f) each piston is fitted into the rear opening of each component chamber until its front end contacts the sealant or immerges into the still soft sealant.

In a ninth aspect, the invention relates to the use of a capsule according to the invention, each chamber containing the allocated component, with an applicator having:
- a plunger which is advanced when the applicator is actuated, and
- means which are used for coupling the capsule in such a way that the plunger can be pushed into the cartridge from the rear.

It may be provided that the material is a material with low to medium viscosity, preferably a dental impression material or a dental temporary restoration material.

It may be provided that the material is a material with high viscosity, preferably a dental filler material.

It may be provided that the material is a material consisting of liquid and/or pasty components.

It may be provided that the two chambers lie next to one another.

The material can be a dental material.

It may be provided that the cartridge is made from a different material than the housing.

It may be provided that the cartridge is made from a different material than the piston.

It may be provided that the housing is made from a different material than the piston.

It may be provided that the first piston is connected to or formed in one piece with the second piston.

It may be provided that at least one of the pistons is connected to or formed in one piece with at least one of the cartridges.

It may be provided that at least one of the component chambers has at least one opening closed by a seal.

It may be provided that the seal is a film attached to the cartridge.

It may be provided that the seal is formed in one piece with the cartridge.

It may be provided that the seal is a membrane formed in one piece with the cartridge.

It may be provided that the capsule comprises a piercing member for piercing the seal.

It may be provided that the first component chamber has a rear opening closed by the first piston.

It may be provided that:
the first piston has a front end;
the first component chamber has a rear opening for receiving the first piston;
the front end is connected to or formed in one piece with a part of the cartridge surrounding the rear opening and closes the rear opening.

It may be provided that the connection between the piston and the cartridge forms a breaking line which enables the parts to be disconnected upon advancing the piston.

It may be provided that the first component chamber has a rear section holding a plug.

It may be provided that the plug is formed in one piece with a part of the cartridge surrounding the rear section.

It may be provided that the plug is made from a different material than the cartridge.

It may be provided that the plug comprises a through hole running from the outside to the inside of the first component chamber.

It may be provided that:
the plug has a rear face;
the plug comprises a filling nipple protruding from the rear face;
the through hole runs through the filling nipple.

It may be provided that the capsule comprises a stopper for closing the through hole.

It may be provided that the plug has a front face with a funnel shaped surface leading to the through hole.

It may be provided that:
the plug is made from an elastic material;
the through hole is collapsed at least when the plug sits in the first component chamber.

It may be provided that:
the cartridge comprises an outer wall with a cylindrical outer surface;
the cartridge chamber comprises a cylindrical inner surface facing the outer surface when the cartridge is held in the cartridge chamber;
a tongue and groove joint is provided on the outer surface and the inner surface.

It may be provided that:
the cartridge comprises a partition wall between the first component chamber and the second component chamber;
the groove of the tongue and groove joint runs along the line where the partition wall meets the outer wall.

It may be provided that at least the outer wall of the cartridge is made from a material containing at least one nano filling substance. For example, by adding a suitable nano filling substance the oxygen permeation through the outer wall of the cartridge may be increased while maintaining the water vapor barrier so that an anaerobic or oxygen-free polymerization of a component contained in the component chamber adjacent this outer wall, may be prevented.

It may be provided that at least the outer wall of the cartridge is made from a generally transparent material which is opaque for certain wave length. One example is a transparent orange material which is opaque for blue light.

It may be provided that:
at least the first component chamber has a rear section holding a permeable piston which is permeable to air but impermeable to the first component;
the permeable piston has a front face contacting the first component contained in the first component chamber.

It may be provided to use a ball, especially an elastic ball (e.g. made out of rubber) as piston. A ball may provide optimum sealing as well as advantages during assembly (no correct positional arrangement necessary). Furthermore a ball provides an enforcement of the sealing when pushed by the plunger, as it is compressed in length and therefore increases in diameter thus enforcing the contact pressure of the sealing.

It may be provided that the capsule comprises a snap-fit lock to ensure that the cartridge does not migrate rearwards when the paste is dispensed (since paste can flow under the cartridge at the end). For example, locking hooks can be arranged on the inside of the capsule and snap into corresponding catches on the cartridge as soon as the cartridge is pressed into its front end position. A bayonet-type closure could also be provided between cartridge and capsule.

It may be provided that the capsule contains a pre-mixing chamber which, before the two substance components A and B flow into the static mixer, divides them into several, e.g. four, paste streams A, B, A, B and brings these back together to form two paste streams, which however each consist of at least two different substance components A and B. This can be achieved by each substance component, even as it flows out of the capsule, being divided into two or more paste streams which are then conveyed farther on the capsule end face through a type of labyrinth and are brought together in the above-described manner. The advantage of this is that a pre-mixing chamber cuts down the overall structural length, because the actual static mixer in the cannula can be supplied with already pre-mixed substance and can therefore be made shorter.

It may be provided that substances with nanofillers are used for making the cartridge, e.g. in order to increase the storage stability of the filled substances. For example, addition of nanofillers can increase oxygen permeation through the cartridge wall (e.g. to prevent anaerobic or oxygen-free polymerization of the component adjacent this cartridge wall), while the water vapor barrier is maintained. It is also possible to use plastics and appropriate additives with which thin walls can be injection-molded or with which the opacity of the cartridge can be increased (less protection against light in production).

It may be provided that the component chambers have equal or different cross sections, with respect to both the shape and the size.

It may be provided that the capsule is adapted for use with an applicator having a single plunger.

It may be provided that the cartridge comprises at least two pistons for movement within respective component chambers, wherein each piston has a rear face, wherein the rear faces are adapted to be simultaneously in contact with a single plunger.

It may be provided that the cartridge or the housing comprises connector elements fitting to corresponding connector elements of an applicator.

BRIEF DESCRIPTION OF THE DRAWINGS

FIGS. 43-47 are sectional view of a cartridge which can be sealed at both ends;

FIGS. 48-58 are cross-sectional side views of an alternative cartridge and piston arrangement;

DETAILED DESCRIPTION OF PREFERRED EMBODIMENTS

Preferred embodiments of the invention are described in more detail below with reference to the attached drawings, which are by way of example only.

Figure 1:
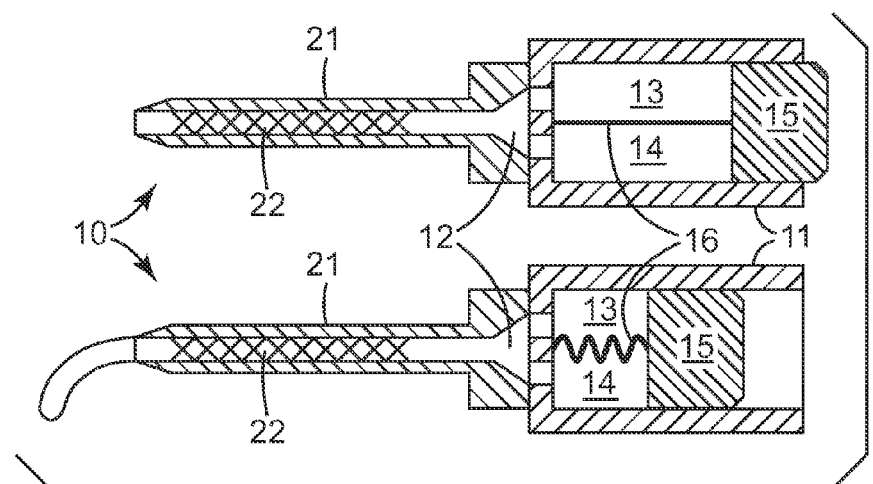
FIG. 1 is a sectional side view of a capsule in a first embodiment.

FIG. 1 shows a capsule 10 in a first embodiment, comprising:
- a cartridge 11 comprising an outlet 12, a first component chamber 13 for containing a first component, and a second component chamber 14 for containing a second component, the two chambers opening into the outlet 12; and
- a piston 15 which at least with its front end sits in the cartridge 11, lies with its rear end outside the component chambers 13, 14 and, when it is pushed forwards, presses the two components out of their component chambers 13, 14.

Each of the two component chambers 13, 14 is separated from the rest of the interior of the cartridge 11 by a common partition wall 16 which is flexible and separates the two chambers from one another. The partition wall 16 is fixed with the rear part of its edge on the front end of the piston 15, and with the remaining part of its edge on the cartridge 11. The partition wall is secured or fixed at least with part of its edge on the cartridge, preferably by adhesive bonding or welding, or by being in one piece therewith.

A cannula 21, in which a mixer 22 is arranged, is mounted on the outlet 12 of the cartridge 11.

Figure 2:
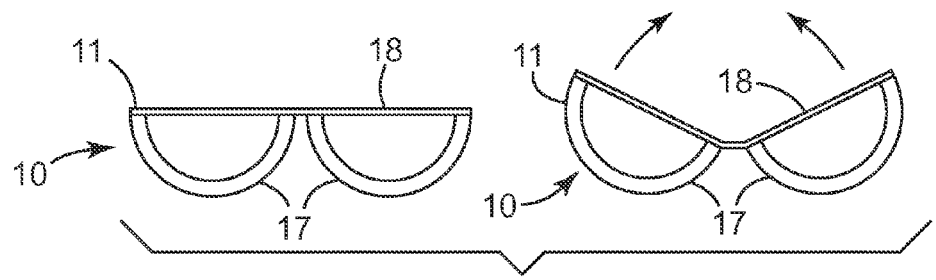
FIG. 2 is a sectional front view of a capsule in a second embodiment, having a divided cartridge.

FIG. 2 shows a capsule 10 in a second embodiment in which:
- the cartridge 11 is divided in the axial direction into two shells 18 for receiving the two components; and
- each of the two shells 17 is closed off by a common foil 18.

The two shells 17 are connected to one another in a foldable manner at two adjoining edges. The two other edges can have corresponding locking means (not shown).

Figure 3:
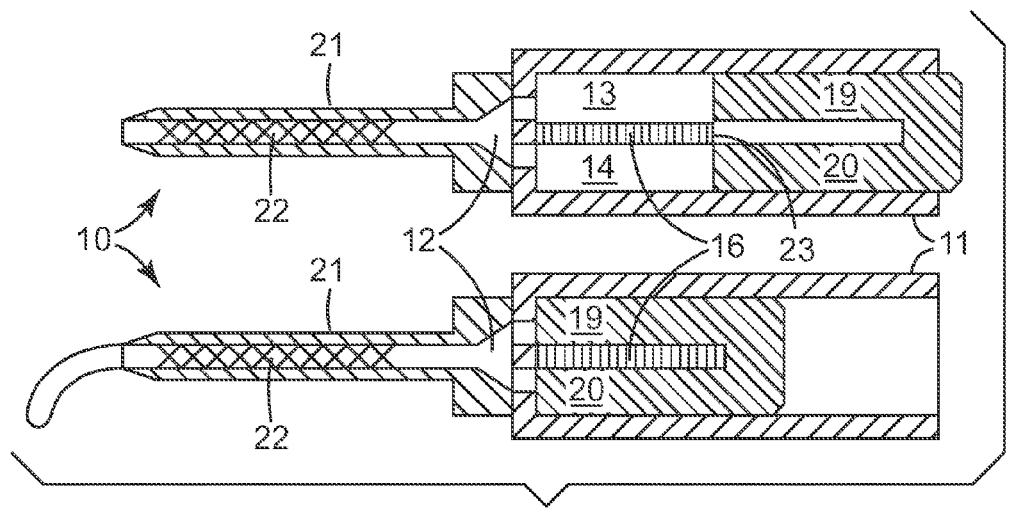
FIG. 3 is a sectional side view of a capsule in a third embodiment.

FIG. 3 shows a capsule 10 in a third embodiment similar to the first embodiment, and the differences will be described in the following.

This capsule 10 comprises:
- a first piston 19 which at least with its front end sits in the first component chamber 13, and a second piston 20 which at least with its front end sits in the second component chamber 14, which two pistons lie with their rear ends outside the component chambers and, when they are pushed forwards, press the two components out of their component chambers.

The common partition wall 16 is rigid and has as can be seen in the upper picture of FIG. 3, a free rear end or edge 23 which sits between the facing sides of the pistons 19, 20 so that it bears laterally on them. The remaining part of the partition wall's 16 edge is in one piece with the cartridge 11.

The two pistons 19, 20 are connected fixedly to one another at their rear ends and are in one piece with each other.

Figure 4:
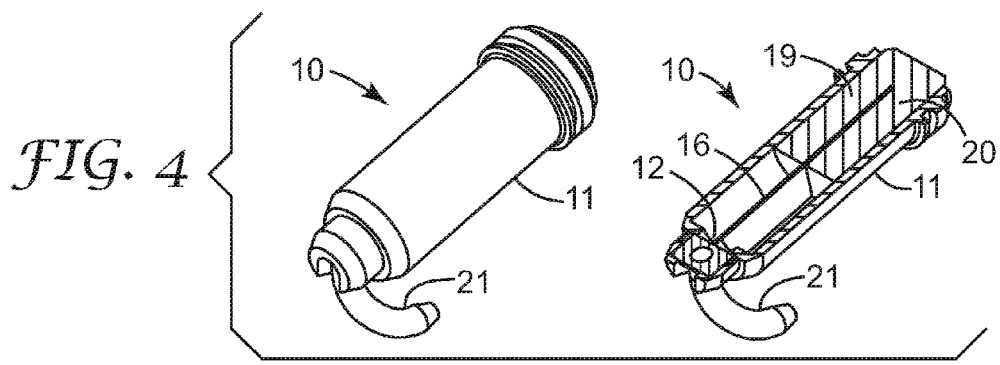
FIG. 4 and FIG. 5 are perspective views and sectional views of a capsule in a fourth embodiment.
Figure 5:
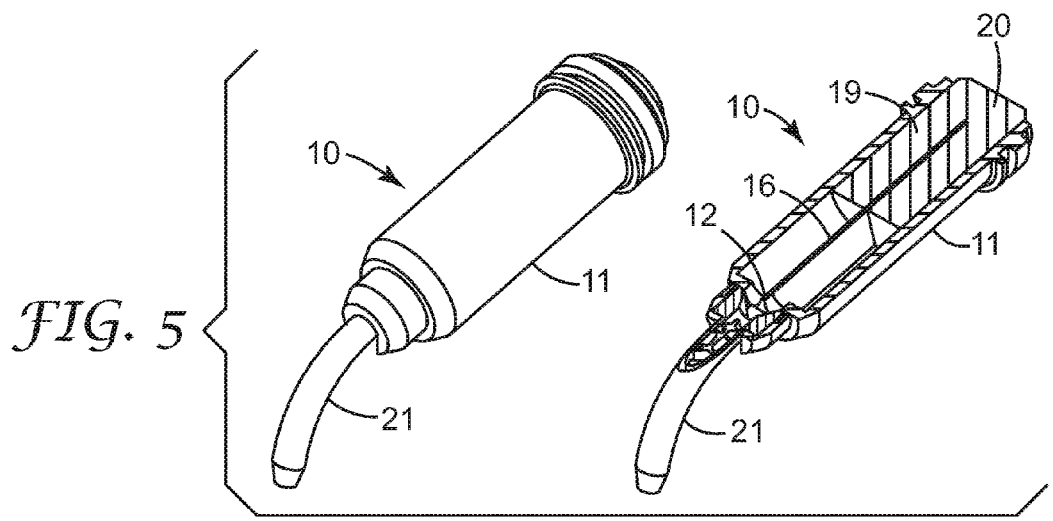

FIG. 4 and FIG. 5 show a capsule 10 in a fourth embodiment similar to the third embodiment, and the differences will be described in the following.

The cannula 21 is mounted pivotably on the cartridge 11 in such a manner that the cannula 21, in a first position (FIG. 4), closes off the outlet 12 of the cartridge 11 and, in a second position (FIG. 5), is connected to the outlet 12 of the cartridge 11.

Figure 6:
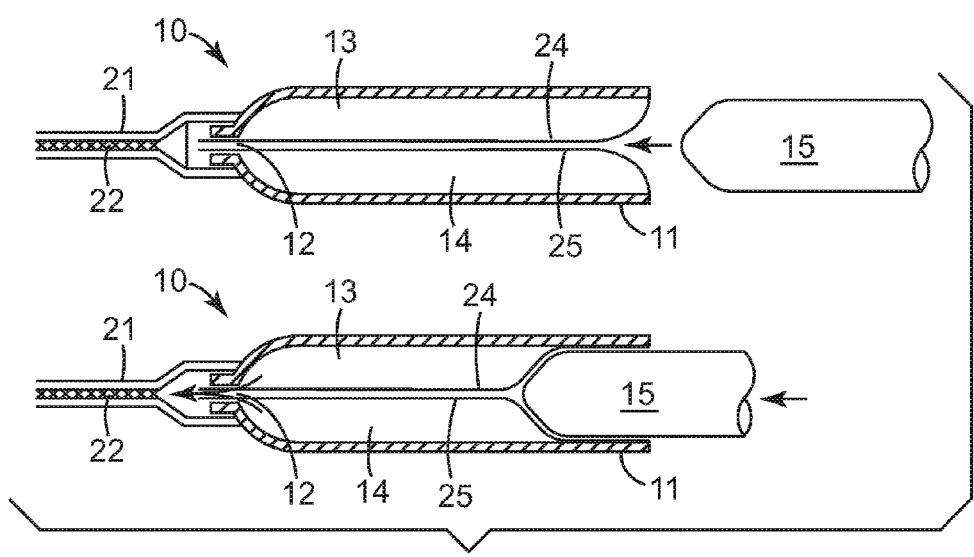
FIG. 6 is a sectional side view of a capsule in a fifth embodiment.

FIG. 6 shows a capsule 10 in a fifth embodiment similar to the above embodiments, and the differences will be described in the following.

A first foil 24 delimits the first component chamber 13 and separates it from the rest of the interior of the cartridge; and a second foil 25 delimits the second component chamber 14 and separates it from the rest of the interior of the cartridge. The piston 15 sits with its front end in the cartridge 11 and lies with its rear end outside the component chambers 13, 14. Each foil 24, is designed as a leaf and is secured or fixed with its edge on the cartridge 11, preferably by adhesive bonding or welding.

Figure 7:
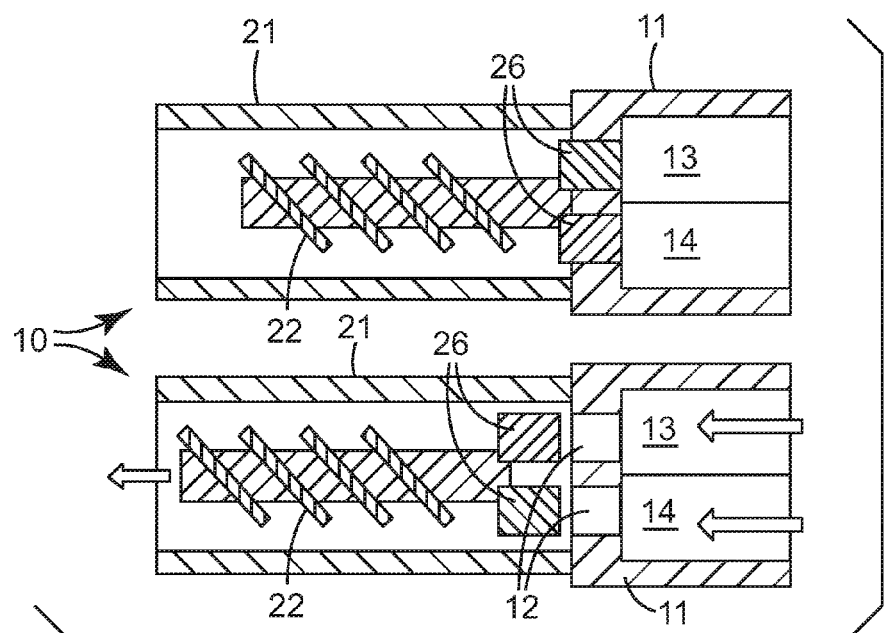
FIG. 7 a sectional side view of a mixer with stopper as closure for the chamber outlets.

FIG. 7 shows a front portion of the cartridge 11 and a rear portion of the cannula 21 and mixer 22. The outlet of the cartridge 11 comprises two outlet openings 12 of the component chambers 13, 14, which are closed off by two stoppers 26 respectively (upper picture). The stoppers 26 are in one piece with the rear portion of the mixer 22 and are pushed forward together with the mixer 12 (lower picture) when pressure is exerted on the components, so that the stoppers 26 free the outlet openings 12.

Figure 8:
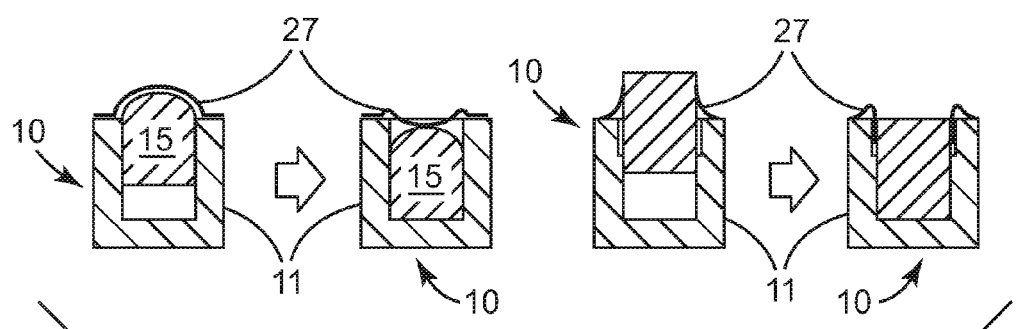
FIG. 8 is a sectional side view of two variants of a sealing foil at the rear opening of the cartridge.

FIG. 8 shows very schematically (e.g. the outlet 12 and the component chambers 13, 14 are not shown) two variants of a sealing for the capsule 10. In both variants, a sealing foil 27 closes off the rear opening of the cartridge 11 and is secured or fixed with its outer edge on the edge of the rear opening of the cartridge 11. Although FIG. 8 shows very schematically only one piston 15, this one is to be understood to represent also the two pistons 19, 20.

In the first variant (upper half of FIG. 8) the sealing foil 27 is designed as a leaf and covers the rear end of the piston 15.

In the first variant (lower half of FIG. 8) the sealing foil 27 is designed as a circular ring and is secured or fixed with its inner edge on the jacket surface of the piston 15.

Figure 9:
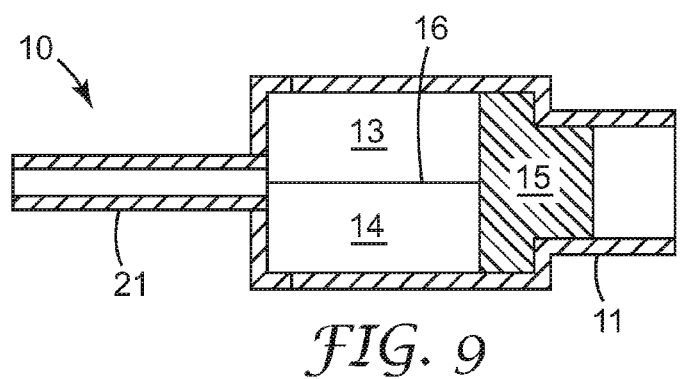
FIG. 9 is a sectional side view of a cartridge with stepped interior wider at the front.

FIG. 9 shows a cartridge 11 similar to that shown in FIG. 1, but having an interior with a stepped diameter, the front area being wider than the rear area. The component chambers 13, 14 are arranged in the front area, and the piston 15 has a jacket surface matching the stepped interior and sits with its front end in the front area and with its rear end in the rear area.

Figure 10:
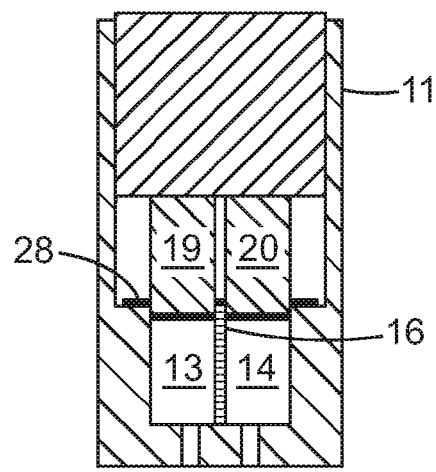
FIG. 10 is a sectional side view of a cartridge with stepped interior narrower at the front.

FIG. 10 shows a cartridge 11 similar to that shown in FIG. 3, but having an interior with a stepped diameter, the front area being narrower than the rear area. The component chambers 13, 14 are arranged in the front area, and a sealing foil 28 is secured or fixed on the circumferential step surface and closes off the rear openings of the component chambers 13, 14. The sealing foil 28 and the pistons 19, 20 are configured in such a way that each piston 19, 20, when advanced into the allocated component chamber 13, 14, pierces the sealing foil 28 about the piston's 19, 20 entire circumference.

Figure 11:
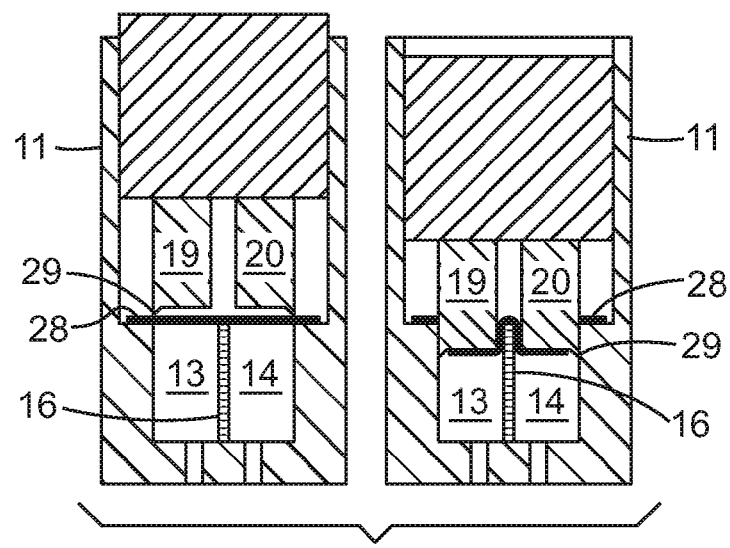
FIG. 11 is a sectional side view of another cartridge with stepped interior narrower at the front.

FIG. 11 shows a cartridge 11 similar to that shown in FIG. 10. Each piston 19, 20 has a piercing tip or piercing edge 29 in the area of the cartridge wall. The sealing foil 28 and the pistons 19, 20 are configured in such a way that each piston 19, 20, when advanced into the allocated component chamber 13, 14, pierces the sealing foil 28 only in the area of the cartridge wall. When advanced farther (right picture), the pistons 19, 20 push the sealing foil 28 toward the partition wall 16.

Figure 12:
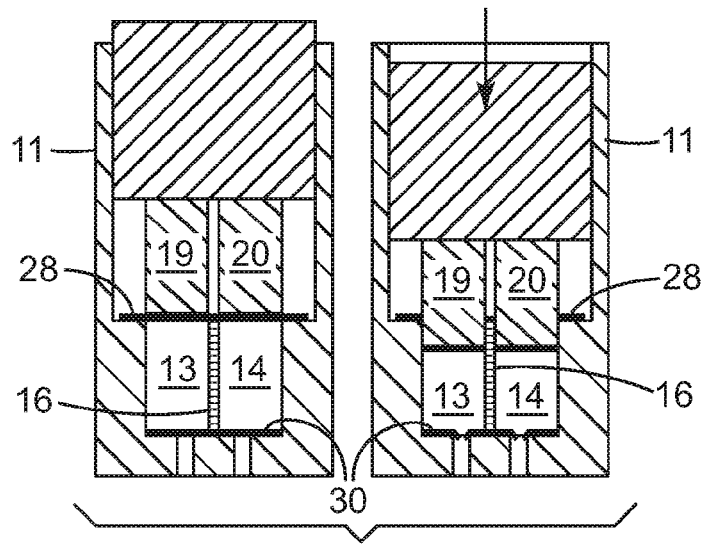
FIG. 12 is a sectional side view of a further cartridge with stepped interior narrower at the front.

FIG. 12 shows a cartridge 11 and pistons 19, 20 similar to those shown in FIG. 10. Each component chamber 13, 14 is closed off at its front end by a sealing foil 30 that breaks (right picture) when the pistons 19, 20 are advanced into the component chambers 13, 14.

Figure 13:
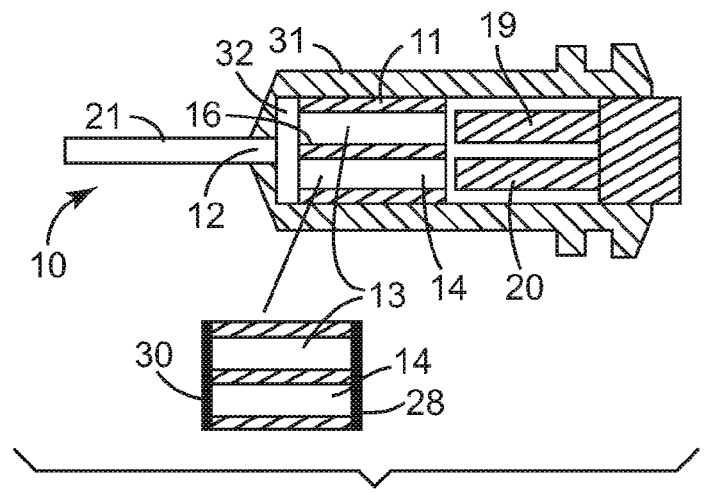
FIG. 13 is a sectional side view of a capsule in a sixth embodiment, having a housing holding the cartridge.
Figure 14:
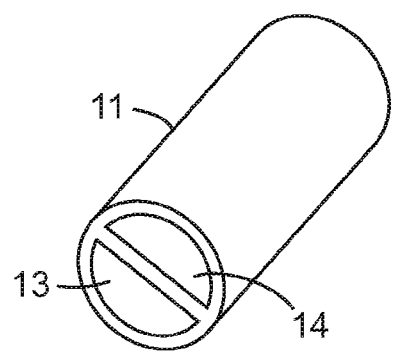
FIG. 14 is a perspective view of a cartridge for the capsule of FIG. 13.

FIG. 13 and FIG. 14 show a capsule 10 in a sixth embodiment, comprising:
- a cartridge 11 comprising a first component chamber 13 for containing a first component and a second component chamber 14 for containing a second component;

a body or housing 31 comprising an outlet 12 and a cartridge chamber 32 for holding the cartridge 11, the cartridge chamber 32 being connected to the outlet 12;

a first piston 19 for movement within the first component chamber 13, and a second piston 20 for movement within the second component chamber 14.

The body or housing 31 (FIG. 13) is a hollow cylinder (without partition wall) for receiving a two-chamber or multi-chamber container or cartridge 11 in the cartridge chamber 32 (FIG. 14), the capsule 10 thus being in two parts. It is advantageous here that the container or cartridge 11 can be designed to permit optimal aging stability of the pastes, while the capsule 10 and/or the housing 31 includes further functional elements.

The container used is preferably a cylindrical cartridge 11 (FIG. 14) with two or more channels or chambers 13, 14 which are arranged on the longitudinal axis of the cylinder and receive the pastes. Optionally, it is possible to use an individual cartridge for each paste component. This provides advantages in manufacturing pastes with several colour shades: one component contains the different shades, while the other always has the same composition and can be produced in larger batches.

It is also advantageous that the cartridge 11 can be made of a material which is optimized in respect of the storage of the substance with which it is filled, while the housing 31 can be configured with design or labeling requirements in mind. For example, the housing 31 can be colour-coded depending on the type of filling material (e.g. a filling material for different tooth colours). The cartridge 11, however, can be made of the same material for all substance types, e.g. can be transparent in order to avoid colour penetration into the substance with which it is filled. Or it can be made of dark material in order to take account of the photosensitivity of the substance with which it is filled.

A cartridge 11 designed in this way can be easily sealed off with foils 28, 30 at its ends (lower picture in FIG. 13).

Instead of the sealing foil 28 on the cartridge's 11 rear end, this rear end can be closed off with a membrane formed integrally with the cartridge 11 (e.g. injection-molded).

Figure 15:
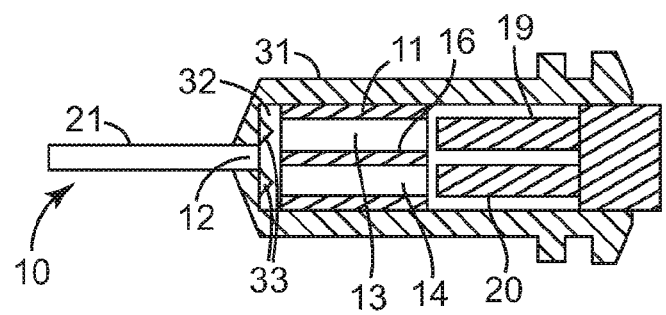
FIG. 15 is a sectional side view of a capsule in a seventh embodiment, having piercing elements.

FIG. 15 shows a capsule 10 in a seventh embodiment similar to the sixth embodiment, and the differences will be described in the following.

The arrangement of the housing 31 receiving the cartridge 11 affords in particular the possibility of a self-opening mechanism for the front end of the cartridge 11. For example, as shown in FIG. 15, the inside of the housing 31 can have piercing elements 33 for the cartridge 11. When the plunger 63 of the applicator 62 presses on the pistons 19, 20, said pistons 19, 20 are moved together with the cartridge 11 towards the piercing elements 33, whereupon the front foil 30 is punctured. The piercing elements 33 can effect initial piercing of the foil 30, so that the foil 30 tears as the paste is advanced.

The piercing elements 33 are here connected to the housing 31, but it may also be provided that they are formed integrally therewith or connected to or formed integrally with the mixer 22 and/or the cannula 21.

Figure 16:
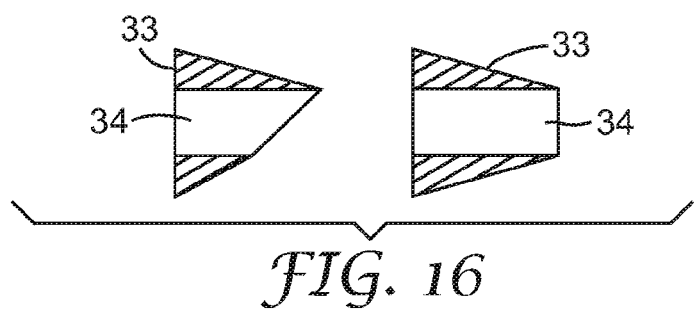
FIG. 16 is a sectional side view of piercing elements in two variants with an internal channel.

FIG. 16 shows two variants of piercing elements 33 with an internal channel 34 through which the pastes flow forwards to the cannula 21.

Figure 17:
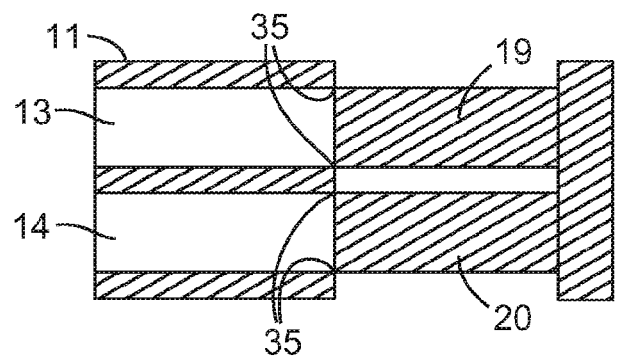
FIG. 17 is a sectional side view of an assembly of cartridge and pistons.

FIG. 17 shows a cartridge 11 and pistons 19, 20 similar to those shown in FIG. 13, but forming together an assembly by being formed integrally with each other. This assembly may for example also be achieved by forming them in a two-component injection-molding process.

Here, the connection 35 between cartridge 11 and each piston 19, 20 is designed such that it ruptures when the respective piston 19, 20 is advanced. This can be achieved by making the connection 35 between the respective parts very thin, e.g. the pistons 19, 20 can be connected to the chambers 13, 14 only at the edges of these parts.

Figure 18:
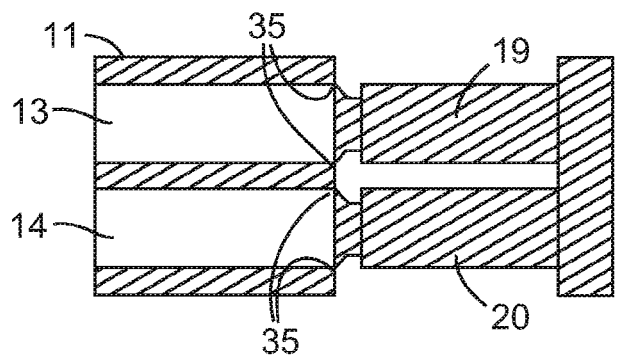
FIG. 18 is a sectional side view of another assembly of cartridge and pistons.

FIG. 18 shows another assembly of cartridge 11 and pistons 19, 20 similar to that shown in FIG. 17, but here the front portion of the pistons 19, 20 has a different shape as shown.

Figure 19:
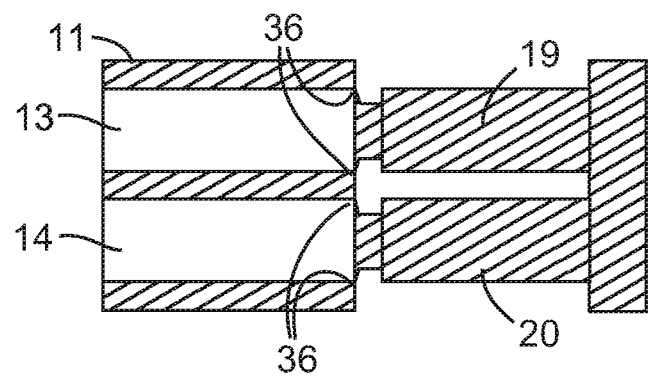
FIG. 19 is a sectional side view of a further assembly of cartridge and pistons.

FIG. 19 shows a further assembly of cartridge 11 and pistons 19, 20 similar to that shown in FIG. 18, but here the parts 11, 19, 20 are connected to one another by a thin membrane 36.

With a predetermined breaking point of suitable design, this breaking point could be used to advantage. If pistons 19, 20 and cartridge 11 are connected to one another via a thin membrane 36, the latter is expanded before breaking, so that the shape of the membrane 36 is slightly greater than the cross section of the chambers 13, 14. In this way, the membranes 36 act as sealing elements when the pistons 19, 20 are advanced. The sealing effect can also be assisted by suitable shaping of the membrane 36, e.g. as an umbrella or circular lip seal in such a manner that the sealing effect increases with increasing pressure.

Figure 20:
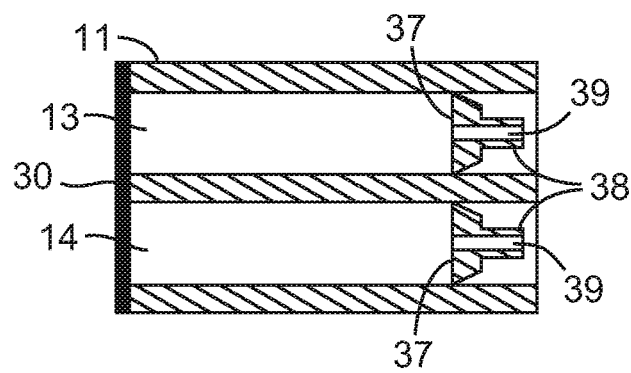
FIG. 20 to FIG. 22 are sectional side views of a cartridge with plugs.
Figure 21:
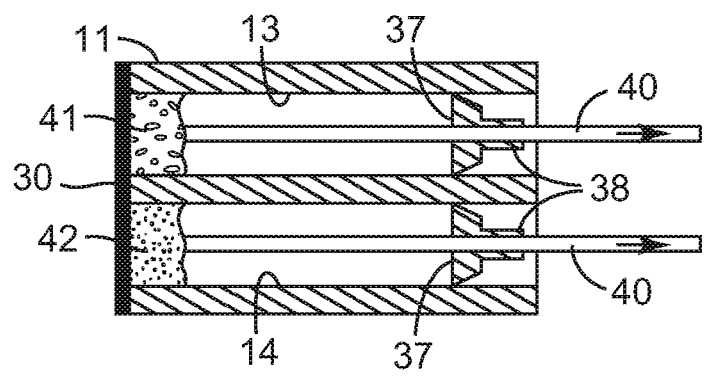
Figure 22:
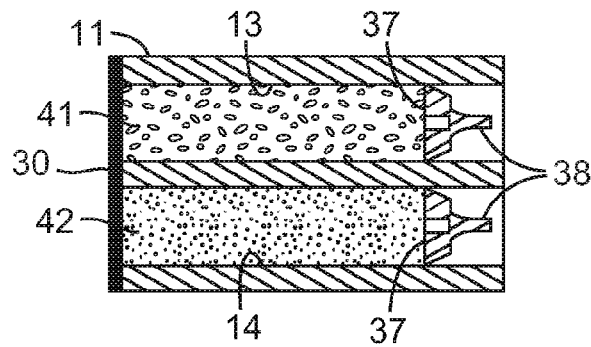

FIG. 20 to FIG. 22 show a cartridge 11 provided with detachable closures, e.g. plugs 37. The plugs 37 have filling nipples 38 extending from their rear faces, and are preferably formed integrally with the cartridge 11. A through-bore 39 allows the cartridge 11, already sealed at the front end by foil 30, to be filled via the plugs 37, e.g. by immersion filling, the metering or filling needles 40 (FIG. 21) lying at the filling level of the substance used for filling, i.e. first component 41 and second component 42. Vacuum filling can alternatively be used instead of immersion filling.

After the filling procedure, the filling nipples 38 are closed off (FIG. 22), e.g. by squeezing with heated or unheated tools. The squeezing can be done using tools with two, three or more jaws. This ensures that the filling procedure is carried out free from air bubbles. Instead of squeezing, it is also possible to seal the filling nipples 38 by a (e.g. heated) wire loop, so that, instead of a wide seal seam, a substantially round pressing is obtained. Alternatively, the filling nipples 38 can be closed by twisting them. The nipples 38 are preferably heated for this purpose. Sealing would also be possible if the inner surface of the nipple 38 is contaminated with paste (depending on the filled paste).

Figure 23:
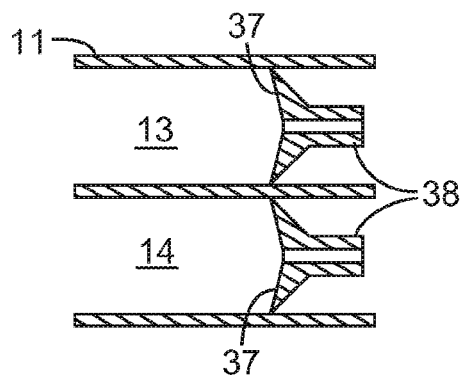
FIG. 23 is a sectional side views of plugs with conical ends.

FIG. 23 shows plugs 37 that are made conical at the end so that the filled substance can flow without forming air inclusions.

In one option, the cartridge 11 can be made of elastic material, and thus the nipple 38 too can be made elastic. It is advantageous that the closures 37 do not have to be provided with open through-bores 39, but can be punctured with pointed filling needles 40. After removal of the filling needles 40, the openings 39 close automatically. It is also possible for the cartridge 11 to be injection-molded from rigid material and for the closures 37 to be injection-molded from elastic material in the two-component injection-molding process.

Another option is for the cartridge 11, unsealed at the front, to be filled from the front end. In this case, openings are not necessary in the closures 37. After the cartridge 11 has been filled, it is closed by a thermally applied, e.g. heat sealed, sealing foil 30 or by an adhesive sealing foil 30.

Figure 24:
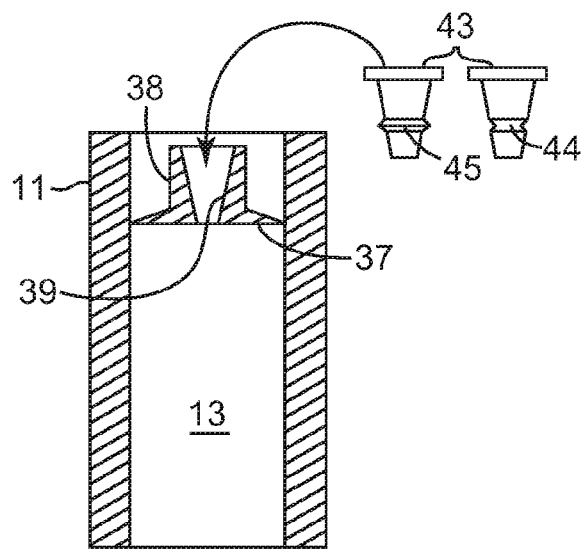
FIG. 24 is a sectional side views of a plug with a stopper.

FIG. 24 shows a plug 37 in the first component chamber 13. Instead of sealing the closure nipple 38, here the filling bore 39 is closed with a stopper 43. The stopper 43 can contain an overflow volume 44 (cf. right stopper) so that, when pressed into the filling bore 39, it displaces substance, which is taken up by the overflow volume 44, and thus closes free from air. It is possible to seal the stopper 43, e.g. by ultrasound. For ultrasonic welding, it is possible to provide energy flow directors 45 in the form of bulges or ridges (cf. left stopper).

Figure 25:
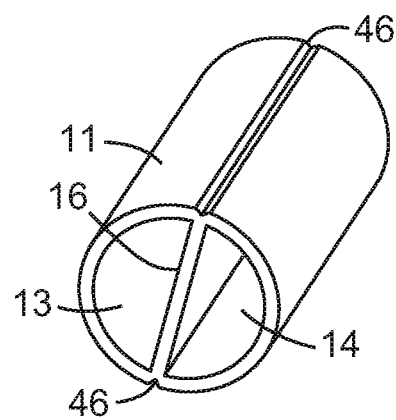
FIG. 25 and FIG. 26 are perspective views of other cartridges with a groove.
Figure 26:
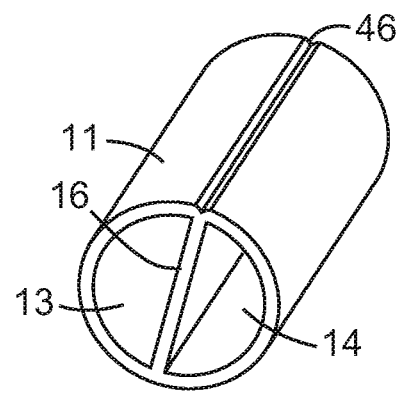

FIG. 25 and FIG. 26 show two further variants for the cartridge 11. In order to orient the cartridge 11 in the housing 31, the cartridge 11 can be provided with at least one notch or groove 46, preferably along the line nearest to the partition wall 16 on the outer wall or shell of the cartridge 11. It is advantageous here that the natural sink marks (FIG. 25) arising in the injection-molding process can simultaneously be avoided or used as positioning groove 46. Moreover, by arranging the groove 46 in the area of the partition wall 16, influences on the permeation properties of the cartridge 11 are substantially avoided. Optionally, it is possible to provide just one groove 46 (FIG. 26), resulting in a more distinct orientation of the cartridge 11 with respect to the housing 31. Alternatively, a raised bridge or key can be arranged on the cartridge 11. Both bridge or key and groove 46 can extend along the entire length of the cartridge 11 or only along part of its length. The housing 31 has the geometrical counterpart which engages in the groove 46 of the cartridge 11 or which receives the bridge or key on the cartridge 11.

Figure 27:
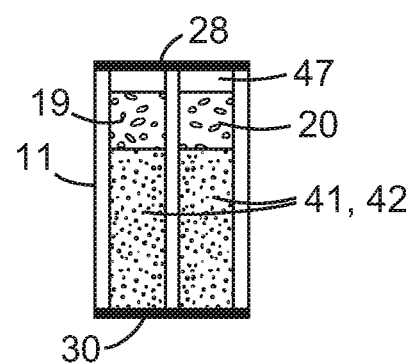
FIG. 27 is a sectional side view of a further cartridge and a sintered piston.

FIG. 27 shows a cartridge 11 having the chambers 13, 14 sealed at one end (by foil 30) and filled to a defined level and then closed with pistons 19, 20. This permits an air-free filling of the cartridge 11. The pistons in this case are designed to be air-permeable, so that the air can escape, while the pistons are pushed into the chambers and therefore no air is trapped in the chambers. The pistons are on the other hand configured in such a way that they are impervious to the paste located in the chambers. Possible solutions in this respect are pistons made of sintered materials, open-pore foams, or small openings in the pistons.

After fitting the pistons, the cartridge is sealed (by foil 28) in order to ensure the necessary storage stability.

If the filled substances require oxygen during storage, the chambers can be extended in length so that a hollow space 47 is obtained between the rear end of the piston 19, 20 and the sealing foil 28.

Figure 28:
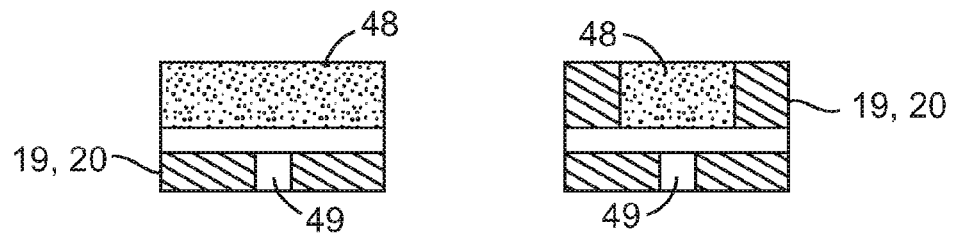
FIG. 28 is a sectional side view of other sintered pistons.

Optionally, sintered pistons 19, 20 can be combined with the hotmelt sealing principle. In a preferred embodiment shown in FIG. 28, the pistons 19, 20 are only partially porous, as shown at the porous sinter part 49, and have channels 49 for injection of a sealing material (hotmelt 64). Such pistons can be produced for example by compaction of the sintered material 48 (optionally under the action of heat), by two-component injection-molding, or by foils sealed on at the ends. After the pistons have been fitted into the chambers 13, 14 filled with dental substance, these are sealed off by injection of the sealing material. During fitting of the pistons, the channels 49 are still open, so that when the pistons are moved into the chambers, the displaced air can escape through the porous sinter layer 48 and the channels 49.

Figure 29:
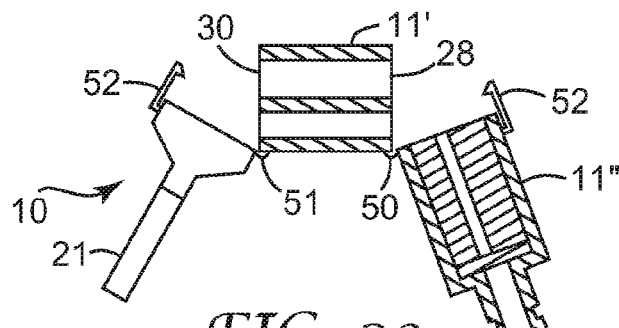
FIG. 29 and FIG. 30 are sectional side view of a capsule in a seventh embodiment.
Figure 30:
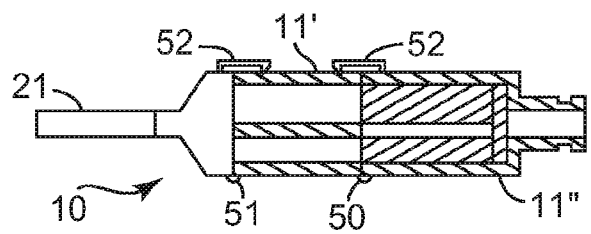

FIG. 29 and FIG. 30 show a capsule 10 in a seventh embodiment, comprising a cartridge 11 having a front or container part 11' and a rear or piston part 11", and further comprising a hinge 50 connecting these parts 11', 11". This permits a stepped capsule design (small diameter at the rear portion of piston part 11" for receiving it in an applicator 62 (FIG. 69, FIG. 70), large diameter at container part 11' for increasing the filling volume). Further, a sealable part, i.e. the rear face of the chamber part 11' which is closed off with sealing foil 28, is obtained, but the capsule 10 can be injection-molded in one tool. In addition, the capsule 10 is provided with a second hinge 51 connecting the container part 11' with the cannula 21, and like the rear face of the container part 11', the front face of the chamber part 11' too may be closed off with sealing foil 30.

The hinge parts 21, 11', 11" are mounted via non-releasable locking elements 52, preferably two, three or more, arranged on the circumference of the capsule 10.

In general a stepped capsule design with or without hinge option can be used to increase the filling volume of the capsule. In this case the rear end of the capsule, i.e. the rear portion of piston part 11", which is designed for adapting to an applicator 62 (FIG. 69, FIG. 70), is kept unmodified while the diameter of the container part 11' of the capsule can be increased as needed.

Figure 31:
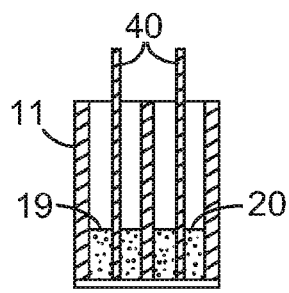
FIG. 31 and FIG. 32 are sectional side views of a cartridge being filled.
Figure 32:
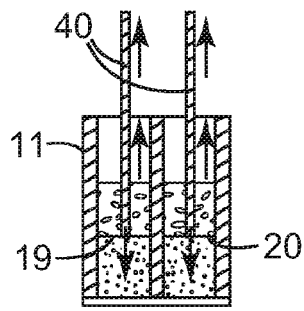

Immersion Filling Through Pistons (FIG. 31 and FIG. 32)

To fill the cartridge 11, the pistons 19, 20 can first be pushed into the chambers until they reach their front end position. The filling needles 40 are then guided through the pistons 19, 20 (FIG. 31). During filling, the pistons are pushed back by the paste pressure and the filling needles are guided back mechanically (principle: immersion filling) (FIG. 32). In this way, inclusion of air in the chambers is avoided. The pistons are preferably made of an elastic material (e.g. rubber), the filling needles piercing through the pistons. After the filling procedure, the filling needles are pulled out, by which means the paste, because of the elastic properties of the piston material, is stripped off from the filling needles. The openings also close automatically because of the elastic properties of the piston material. Nevertheless, the cartridge can be sealed if required, the pistons then also being sealed in. It is in turn possible to provide an air volume between sealing foil and the pistons.

Alternatively, the pistons can be made of less elastic material and can be provided with bores.

Filling from Front End

It is possible for the cartridge/capsule to be filled from the substance outlet end. In this case, it is recommended to fit the pistons in advance (pistons pushed forwards completely). The pistons are then pressed back during filling, if appropriate to a limit stop, so that the chambers are free from air. In this solution too, it is possible to create an air volume behind the pistons if the cartridge/capsule is longer than is necessary for the filling volume and is sealed at both ends.

Air Cushion at Front End of Cartridge/Capsule

It is possible for the cartridge, sealed at one end, to be filled by immersion filling, but not to the brim, and then to seal the second end. The air then enclosed remains at the second end when the filled substances have a high viscosity. If the cartridge is arranged with the "air side" forwards in the capsule, the air is first pressed out when the substance is applied. The substance is then dispensed in exact proportion.

Figure 33:
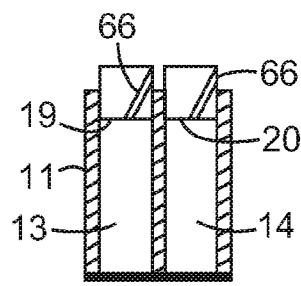
FIG. 33 is a sectional side view of a cartridge having pistons with inclined air vent channels.

Pistons with Inclined Bore (FIG. 33)

A further possibility for air-free filling is provided by pistons 19, 20 with inclined air vent channels 66 (FIG. 33). The channels 66 extend from the front end of the piston 19, 20 to the outer wall or shell of the piston. When the pistons are pressed into the chambers 13, 14, the filled substance can escape outwards through the channels. The piston is sealed off only when it has been pressed in so far that the opening on the shell is located in the chamber. Excess substance can then either be suctioned off or stripped off from the opening. The piston can optionally be pressed still farther into the chamber if the sealing foil is slightly elastic or thermoformed to provide the necessary volume for this.

Figure 34:
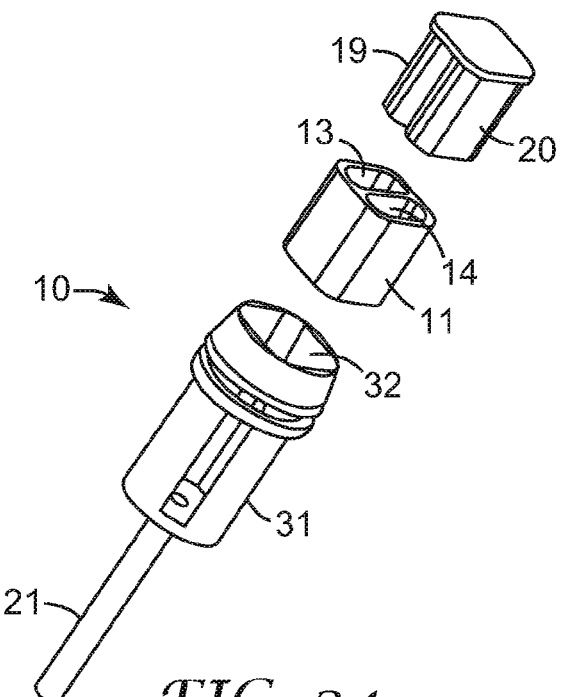
FIG. 34 is an exploded view of a capsule having a substantially square cartridge.
Figure 35:
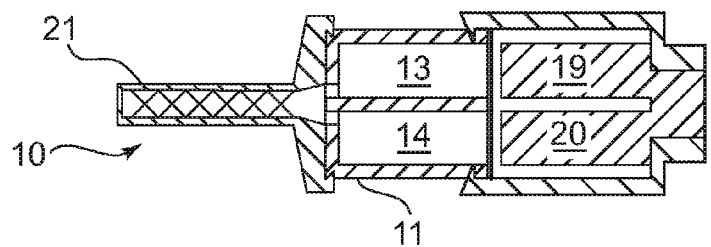
FIG. 35 is a sectional side view of a capsule in which a cartridge replaces the housing.
Figure 36:
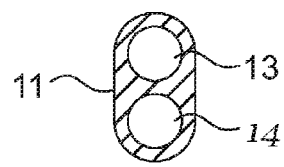
FIG. 36 is a cross-sectional view of a cartridge having chambers.

Optimizing Volume (FIG. 34-FIG. 36)

In an optional variant, the cartridge design deviates from the round shape. In this way, the housing 31 is only partially weakened, instead of the whole wall of the housing 31 being made thin. The aim here is to maintain sufficient mechanical strength of the capsule 10, while the internal volume is increased. Such a solution may be achieved with a substantially square cartridge 11 (FIG. 34). In the area of the cartridge corners, the housing 31 is weakened or broken through, whereas, in the area of the cartridge sides, the capsule wall consists of thick-walled bridges. These bridges take up the application forces during use of the capsule. Optionally, the cartridge 11 can also completely replace the housing 31 (FIG. 35).

In a further design for optimizing the volume of the capsule, the capsule is made wider (FIG. 36). The U-shaped applicator can still be used.

Figure 37:
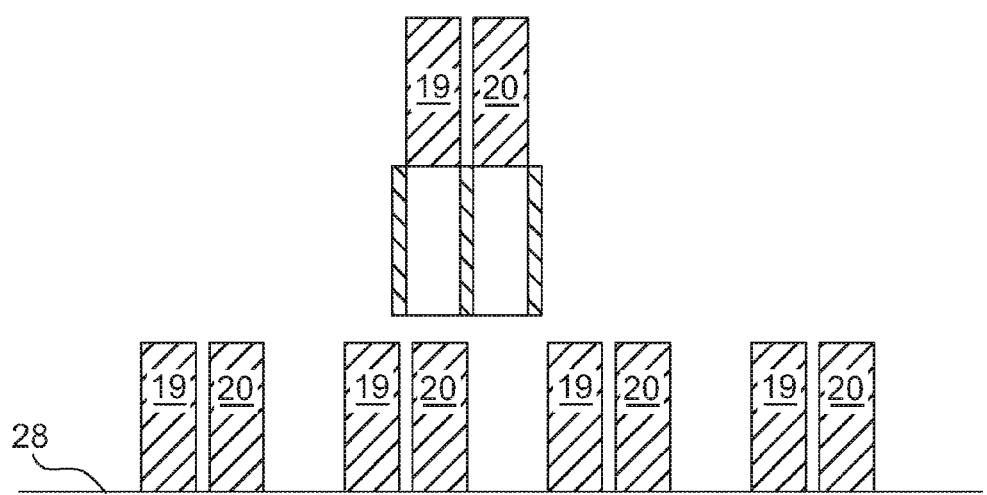
FIG. 37 is a schematic illustration of pistons molded directly onto a sealing foil.

In-Mould Decoration Technique for Assembly of Parts (FIG. 37)

Figure 38:
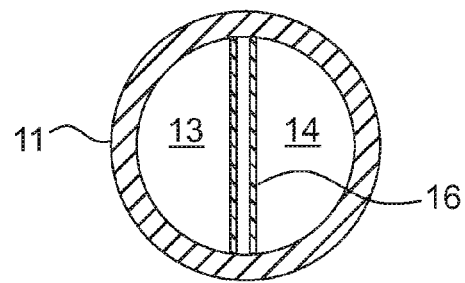
FIG. 38 is a sectional view of an alternate cartridge having a partition wall separating adjacent component chambers.

It may be provided, for example, to injection-mould the pistons 19, 20 directly onto the sealing foil 28 and to use the foil 28 at the same time as a transporter for handling the component parts Air Gap as Diffusion Barrier (FIG. 38)

It may be provided that a partition wall 16 between two adjacent component chambers 13, 14 is designed as a double wall (FIG. 38) in order to reduce permeation of substances between the two chambers 13, 14.

Integral Piston with Hotmelt Closure (FIG. 39-FIG. 42)

Figure 39:
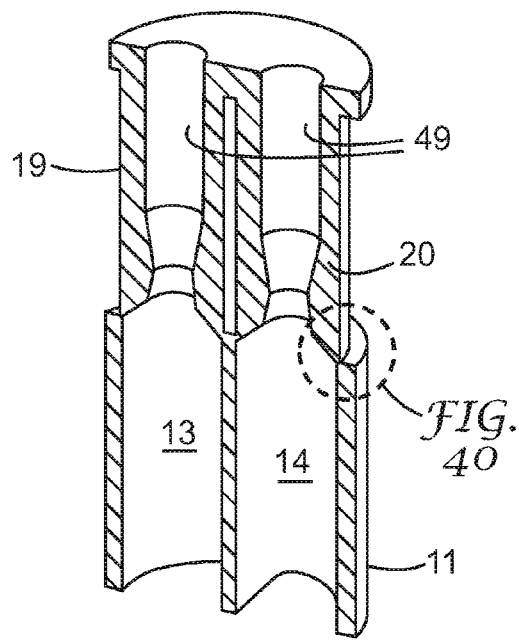
FIGS. 39-42 are sectional side views of a cartridge that may be associated with air-free filling of the substance.
Figure 40:
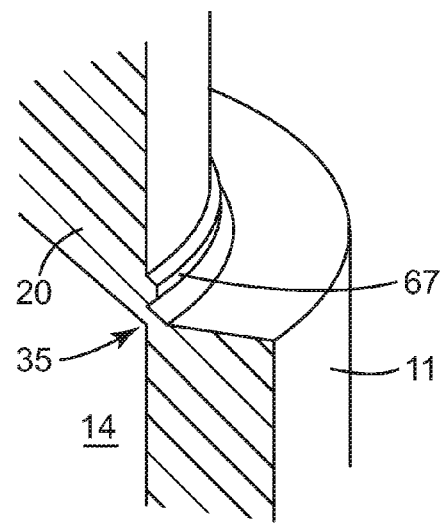

A preferred solution for air-free filling of the substance is illustrated in FIG. 39 to FIG. 42. The cartridge 11 and the pistons 19, 20 are formed in one piece (FIG. 39). Between cartridge 11 and pistons 19, 20 there are predetermined breaking points 35 (FIG. 40) which break upon a defined axial loading of the arrangement. The pistons 19, 20 have an external dimension and shape corresponding approximately to the external dimension/shape of the chambers 13, 14 in the cartridge 11. At their front ends, the pistons 19, 20 preferably have a bead or bulge 67 (FIG. 40) which is slightly overdimensioned in relation to the chambers, while the remaining length of the piston has a slight underdimension (clearance) relative to the chambers.

Figure 41:
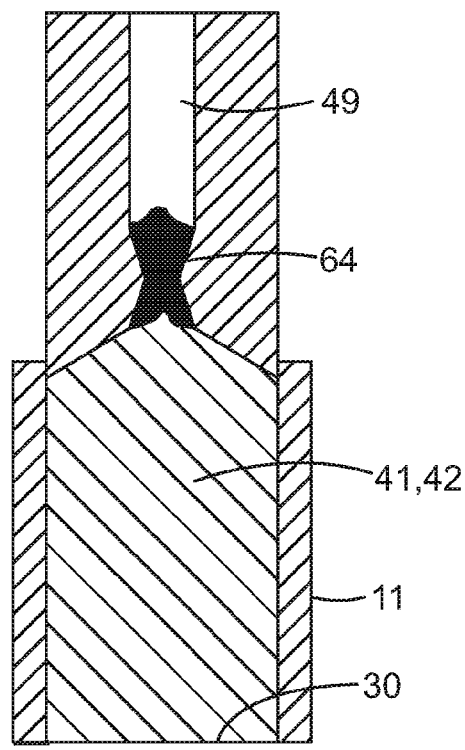
Figure 42:
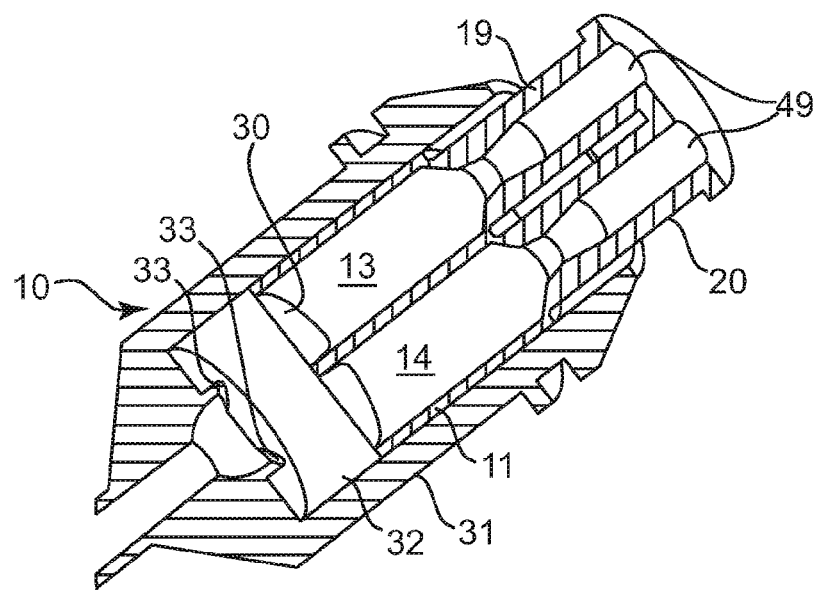
Figure 43:
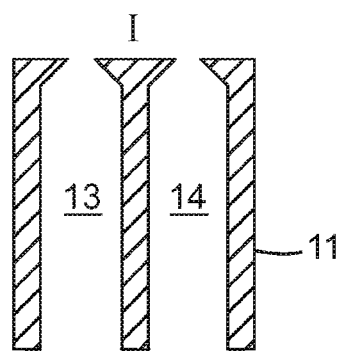
Figure 44:
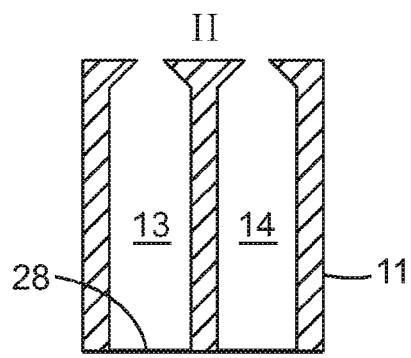
Figure 45:
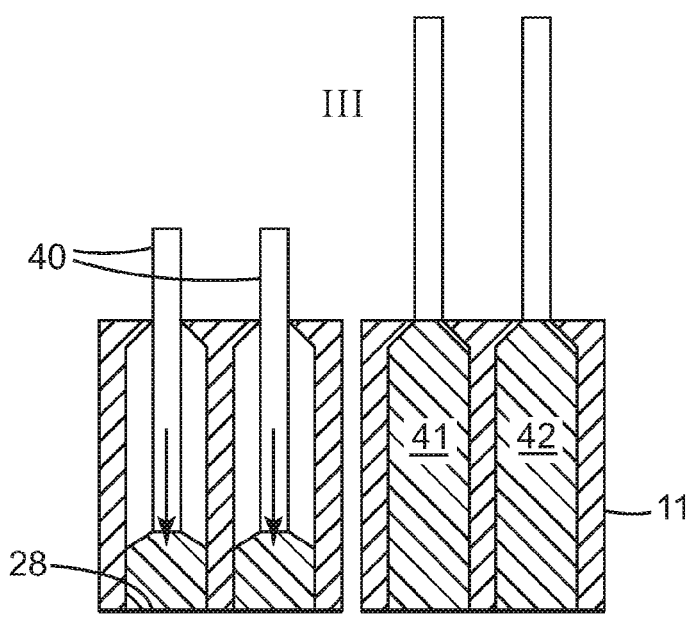
Figure 49:
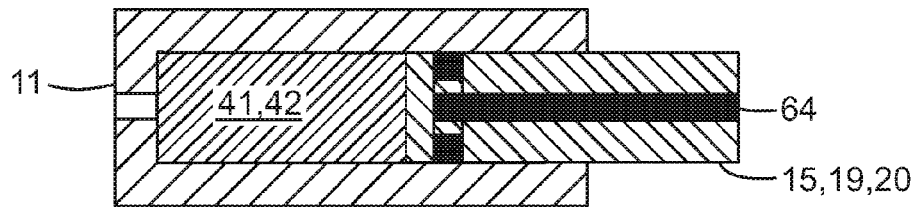

For filling the piston/cartridge arrangement, the cartridge is sealed off at the front with a foil 30. The substance 41, 42 is then introduced through the filling bores or channels 49 by means of immersion filling, starting from the sealing foil 30 and in the direction of the mouth or inner cone of the filling bores or channels 49. The filling level is preferably such that the substance 41, 42 reaches into the mouth or inner cone area of the filling bores or channels 49 (FIG. 41). In a further step, the filling bores or channels 49 are then closed off with a material that can harden (e.g. hotmelt material 64).

The advantage of this method is that filling tolerances of the substance play no role in relation to air-free filling and in relation to exactly proportioned dispensing of the substance by the customer.

In order to ensure optimal stability of the hotmelt closure, the filling bores in the mouth or inner cone area to the cartridge are equipped with a double cone shape. This ensures that the "hotmelt stopper" 64 (FIG. 41) seals by shrinking and that, in the event of excess pressure or low pressure, cannot come loose in the cartridge (e.g. through temperature fluctuations).

The pistons 19, 20 are preferably designed conically or sloping in at the end towards the filling bores or channels 49 (FIG. 42) in order to avoid air inclusions during the immersion filling.

Cartridge which can be Sealed at Both Ends (FIG. 43-FIG. 47)

With the solution shown in FIG. 43 to FIG. 47, a cartridge 11 can be filled free from air and can be sealed without appreciable air inclusions. In this case, the component chambers 13, 14 have, at least at one end, a narrowing cross section (FIG. 43 and FIG. 47) which creates an enlarged sealing surface on the end face of the cartridge 11 (the narrowing cross section will be arranged to the front end side of the housing 31 as the pistons can only penetrate the cartridge from the open side—as an option the cartridge 11 may be arranged in the opposite orientation if it is used together with the embodiment shown in FIGS. 71 and 72). In the filling procedure by means of immersion filling (FIG. 44 and FIG. 45), the minimum filling level is flush with the end face of the cartridge (right picture of FIG. 45), with filling tolerances giving a slight excess. The enlarged sealing surface has the effect that the possible excess, upon application of the sealing foil 30, wets only a very small part of the sealing surface and, together with the rest of the sealing surface, leads to a safe and air-free sealing (FIG. 46).

To fill the cartridge flush with the end face, the filling needles 40 are arranged sealingly in the filling openings so that the air displaced during the filling procedure can escape, whereas the paste cannot easily pass through the gap between the two parts. This results in an abrupt pressure increase in the filling unit as soon as the paste reaches the end of the narrowed chamber area. This pressure increase can be detected by the filling unit, and the filling procedure can thus be automatically ended with precision.

Alternatively, filling can be made flush with the end face by placing the filling needle on said end face of the cartridge, but not into the sealing area.

A combination solution can be provided in which the aforementioned piston with hotmelt closure is arranged at one end of the cartridge and the narrowed area at the other end. This affords advantages in terms of sealing at the front end (larger sealing surface) and one-piece production of the cartridge and of the piston. A preferred production method for this is injection blow molding and subsequent formation of the narrowing because of the difficulty in removing the cartridge interior from the mould.

Sealing the Pistons by Means of Sealing Material (Hotmelt) (FIG. 48-FIG. 58)

In one embodiment, the pistons 15, 19, 20 are provided with channels 49 through which a sealant 64 (hotmelt, adhesive, etc.) can be injected. The pistons can first be fitted after the cartridge 11 has been filled with paste 41, 42, and they can then be sealed off by injecting the sealant. It is advantageous here that the paste can thus be enclosed free from air in the chambers.

In a first variant of the solution (FIG. 48 and FIG. 49), the pistons 15, 19, 20 have an annular groove into which sealant 64 can be injected via a filling channel 49. A seal is thus created between the piston and the inside wall of the chamber. The adhesive is preferably chosen such that it flows easily onto the surface of the chamber and such that it does not form a firm attachment but instead only adheres to the surface. In this way it is possible to move the piston in order to dispense the paste, the sealing material then detaching from the chamber wall (adhesion break) and furthermore acting as a sliding seal. Optionally, the adhesive can be chosen such that it forms a firm connection with the piston and the chamber wall, but itself has a relatively low strength and tears upon displacement of the piston (cohesion break).

Figure 50:
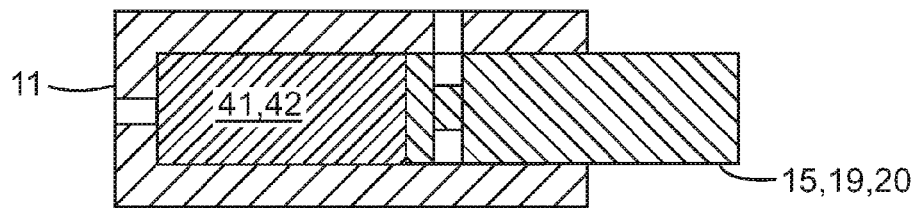
Figure 51:
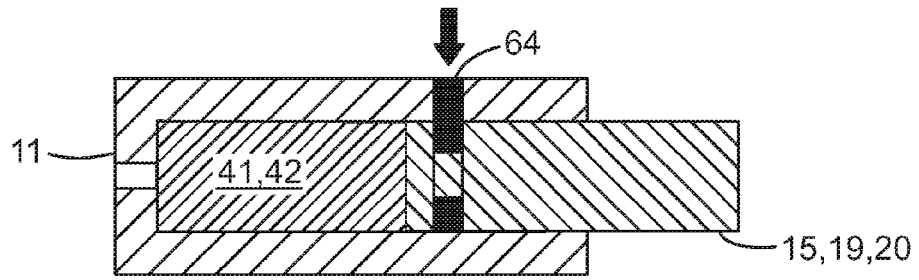

Optionally, the sealing material 64 can also be injected through a filling channel in the capsule wall (FIG. 50 and FIG. 51).

Figure 52:
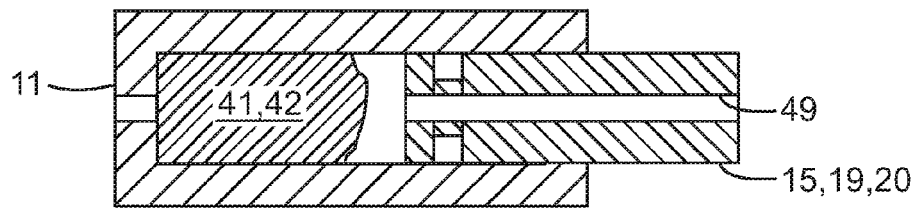
Figure 53:
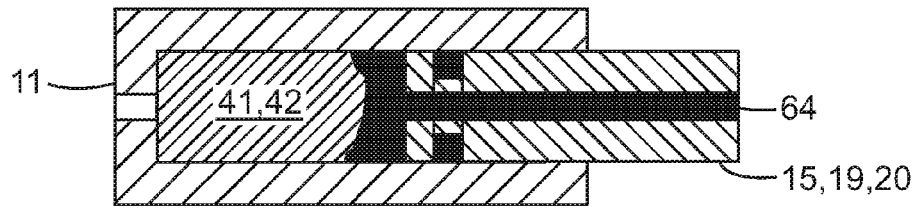

In a second variant (FIG. 52 and FIG. 53), after the piston has been fitted, a hollow space remains between the paste and the end face of the piston (FIG. 52). The filling channel 49 is designed in such a way that, upon injection of the sealing material 64, this space is filled with sealing material and thus provides a stopper-shaped sealing of the chamber (FIG. 53). The annular groove illustrated is optional and serves for further anchoring of the piston or for creating an additional defined seal.

Figure 55:
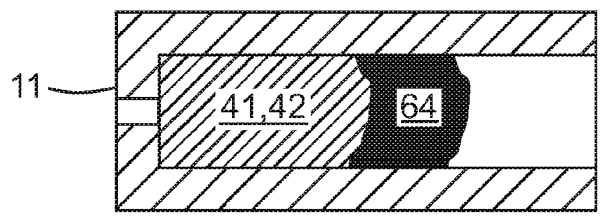
Figure 56:
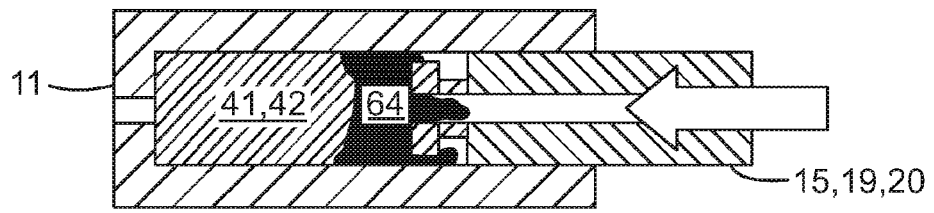
Figure 57:
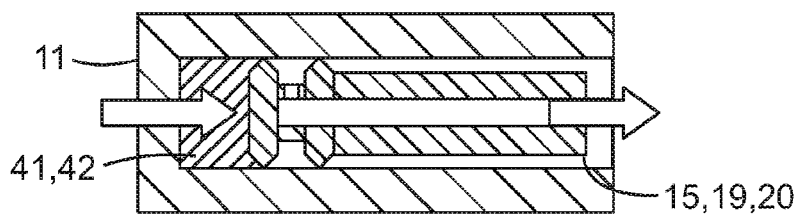
Figure 58:
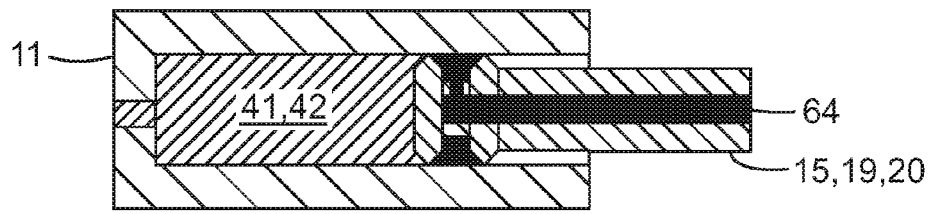

In a third variant (FIG. 54 to FIG. 56), the chamber filled with paste (FIG. 54) is closed off with sealing material, e.g. hotmelt 64, (FIG. 55) and the piston is then fitted into the still soft sealing material (FIG. 56). In this process, the piston does not pass through the sealing material layer. In this way, a simple air-free closure is obtained. Closure of a two-chamber capsule affords the added advantage that the filling level of the paste does not have to be exactly the same in both chambers and the filling level of the sealing material also does not have to exactly correspond. The piston is configured in such a way that excess sealing material can escape in a riser tube arranged in the piston (FIG. 56).

Alternatively, the cooled sealing material could itself serve as a stopper. In this case, the piston would not be pressed into the soft sealing material. The piston would then only be used for transmitting force for advancing the piston.

In a fourth variant (FIG. 57 and FIG. 58), the piston itself has sealing features (e.g. sealing beads or bulges). In this variant, the chamber is preferably filled from the front end of the capsule (FIG. 57), the piston being pushed or drawn back with the paste filling level. In the end position of the piston (FIG. 58), the latter is then fixed and sealed off by a sealing material according to one of the abovementioned methods.

FIG. 59 to FIG. 63 show a capsule 10 in an eight embodiment and related parts thereof.

Figure 59:
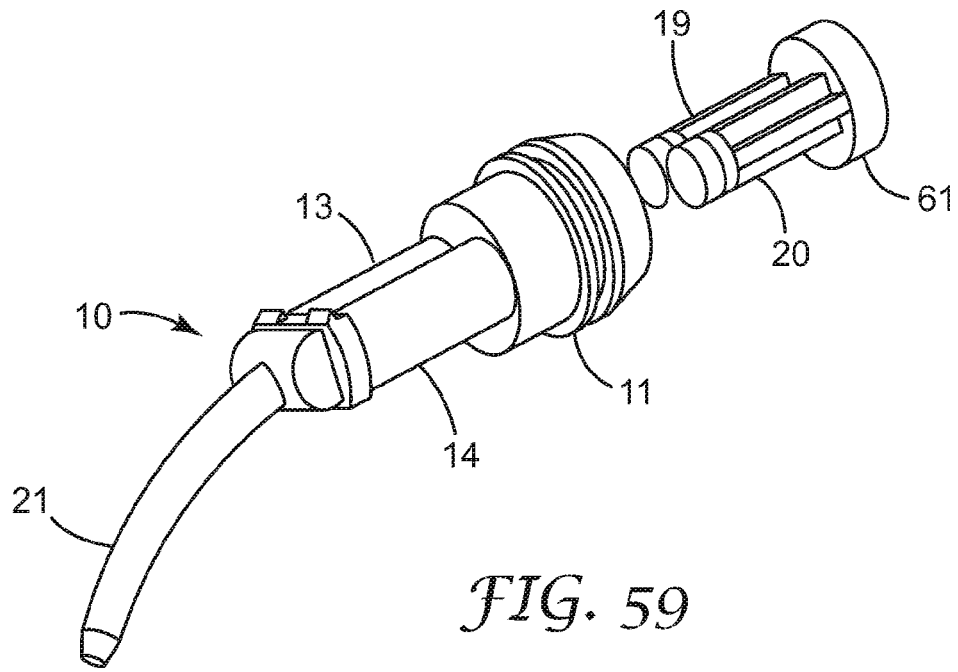
FIG. 59 and FIG. 60 are exploded views of a capsule having a pivoting cannula.
Figure 60:
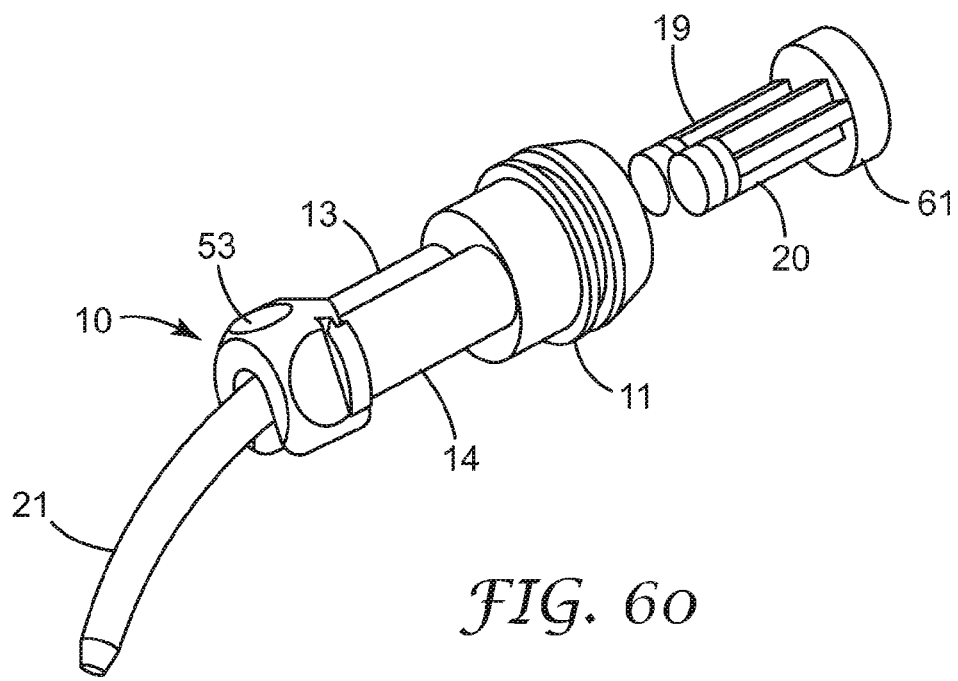
Figure 61:
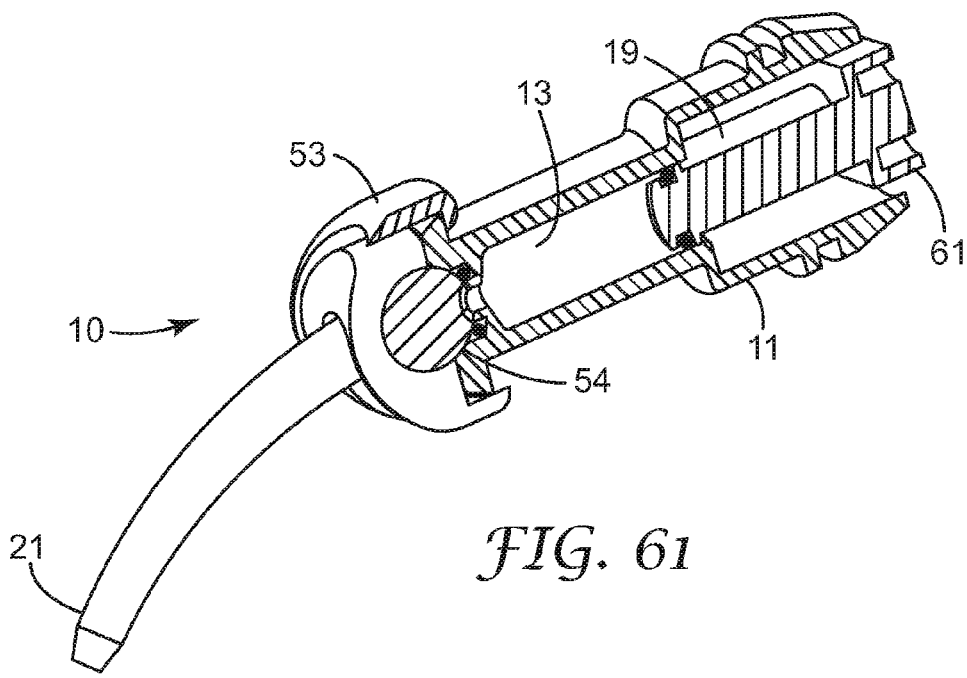
FIG. 61 is a cross-sectional elevated side view of a capsule having a pivoting cannula.
Figure 69:
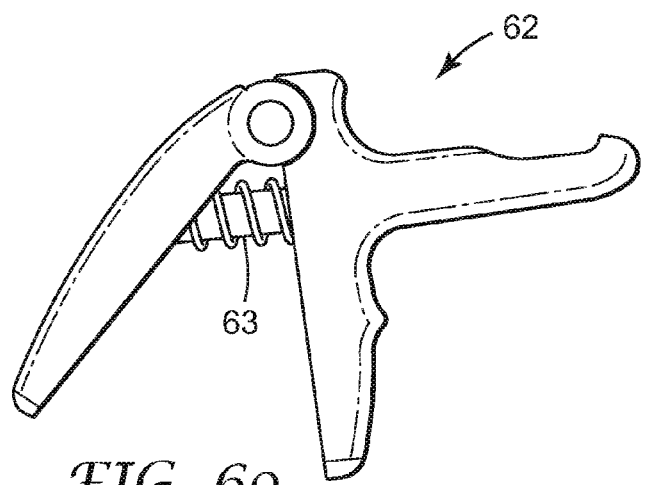
FIG. 69 and FIG. 70 are side views of dispensing applicators.
Figure 70:
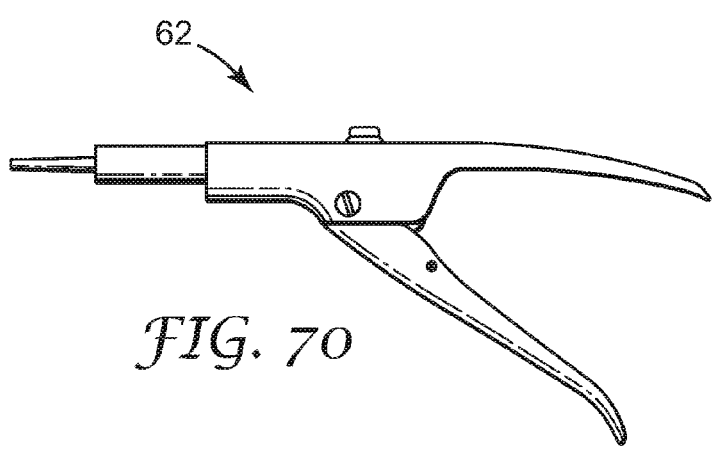

FIG. 59 to FIG. 61 show the capsule 10 comprising the cartridge 11, the pistons 19, 20, the pivoting cannula 21, and a cap 53 for affixing the cannula 21. FIG. 59 shows the capsule 10 before fitting the cap 53, and FIG. 60 shows the capsule 10 after fitting the cap 53. FIG. 61 shows a longitudinal section through the first component chamber 13 and first piston 19. Here, the component chambers 13, 14 and the pistons 19, 20 each have circular cross sections. The pistons 13, 14 are connected at their back ends to a connecting piston having a circular cross section of larger diameter fitting to the diameter of the plunger 63 of an applicator 62 (FIG. 69, FIG. 70).

Figure 62:
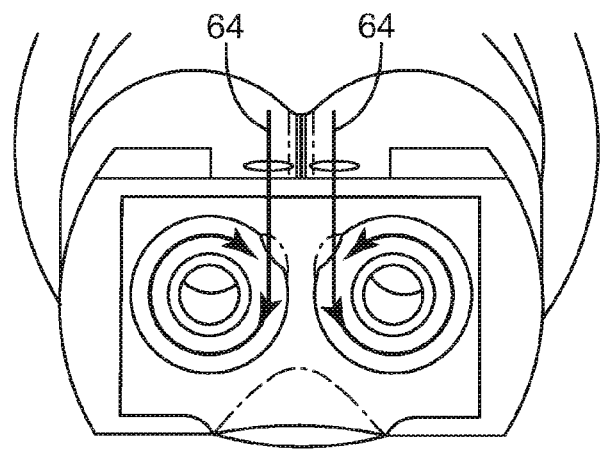
FIG. 62 is a front view of a cartridge having channels.

FIG. 62 shows the front end of the cartridge 11 having channels which are filled with sealing material after the pivoting cannula 21 has been fitted.

Figure 63:
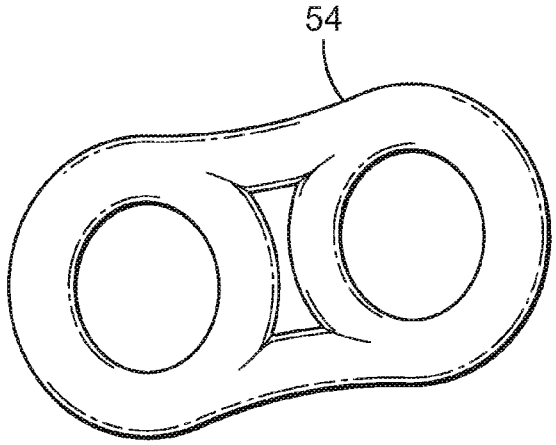
FIG. 63 is a top view of a seal.

A preferred solution for encapsulating the materials in the cartridge 11 and to keep them apart from one another is to close the rear end of the component chambers 13, 14 by plugging with the pistons 19, 20 whereas o-rings mounted on the pistons 19, 20 are used as seals. The front ends of the chambers are closed by the rotatable nozzle or cannula 21 which acts as a valve. As a seal, o-rings are used or a customized rubber seal 60 as shown in FIG. 63.

Figure 54:
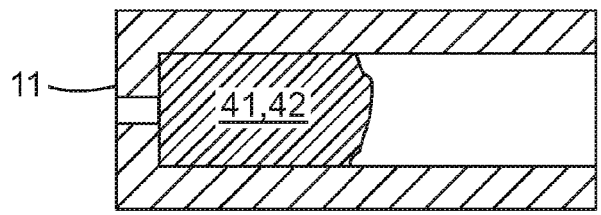

In an optional preferred solution, hotmelt sealing is used, e.g. as described with respect to FIG. 48 to FIG. 58. In these eight embodiments, it is preferred that in a first step the component chambers 13, 14 are filled with the respective components (FIG. 54). In a second step the component chambers 13, 14 are closed off with hotmelt 64 (FIG. 55). In a third step the piston 19, 20 is fitted into the still soft sealing material in a way that it does not pass the sealing material layer (FIG. 56).

Figure 64:
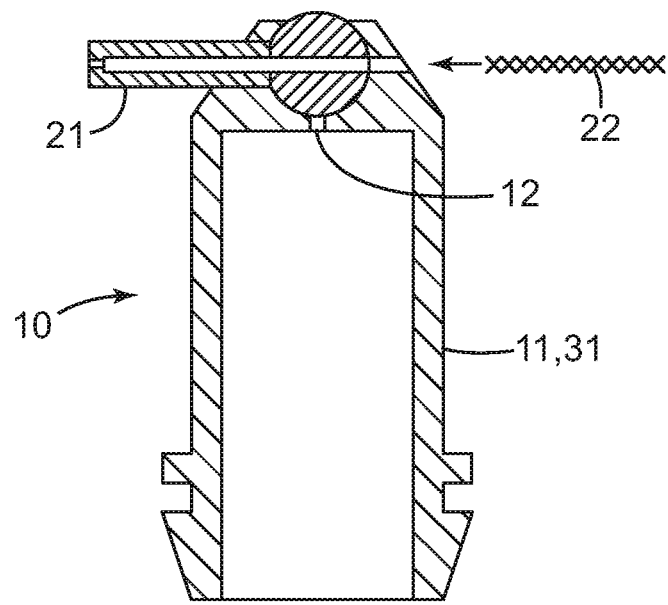
FIGS. 64 and 65 are cross-sectional side views of alternative two-component cartridge assemblies.

Two-Component Injection-Molding with Possibility of Mixer Assembly (FIG. 64)

The embodiment shown in FIG. 64 permits production of the cartridge 11 or housing 31 with pivoting cannula 21 in the two-component injection-molding process, the pivoting cannula 21 preferably being molded first, then the cartridge 11 or housing 31, and the pivoting cannula 21 being encapsulated by the cartridge 11 or housing 31 so that the chambers arranged in the cartridge 11 and intended to receive the dental substance are closed off tight at the cannula side. The plastics used for both parts and the process parameters in the injection-molding procedure are chosen so that, after production, a press-fit between both parts is obtained, and preferably the surfaces of both parts form a detachable connection (light adhesion). The cartridge 11 or housing 31 is thus sealed off tight in the storage condition. Opening of the cartridge 11 or housing 31 is possible, however, by pivoting the cannula 21.

Examples of suitable plastics for the proposed technique are polyolefins, preferably polypropylene, for both parts.

A bore arranged in the cartridge 11 or housing 31 allows the mixer 22 to be fitted on the already injection-molded cartridge 11 or housing 31.

Figure 65:
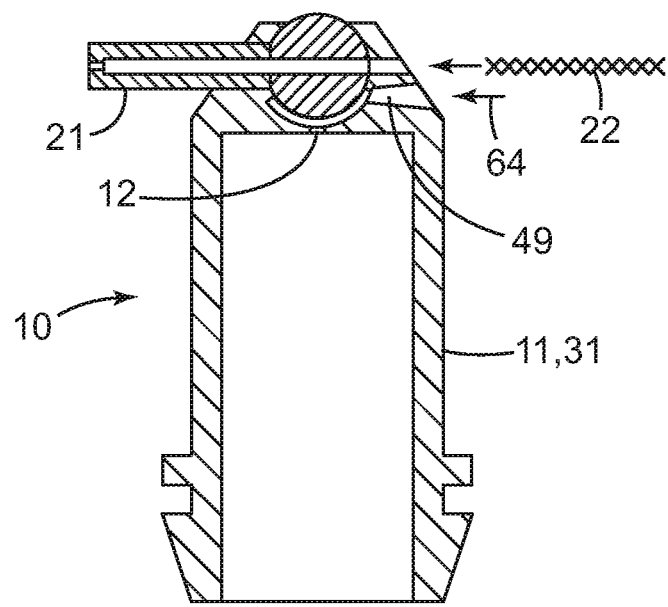

Two-Component Assembly Injection-Molding with Additional Injection-Molded Sealing (FIG. 65)

In the embodiment shown in FIG. 65, cannula and cartridge are produced in a two-component injection-molding process, but without sealing of the substance chambers (assembly injection molding).

Between pivoting cannula and the outlet channel of the cartridge, a hollow space remains which can later be filled with a sealing material. After production, the cartridge is preferably first filled with the dental substance and then closed by injection of the sealing material (e.g. as shown in FIG. 48 to FIG. 56). During the filling of the cartridge with dental substance, the unsealed cartridge end (depending on the filling method) can be used to remove air (FIG. 48 to FIG. 56).

Figure 66:
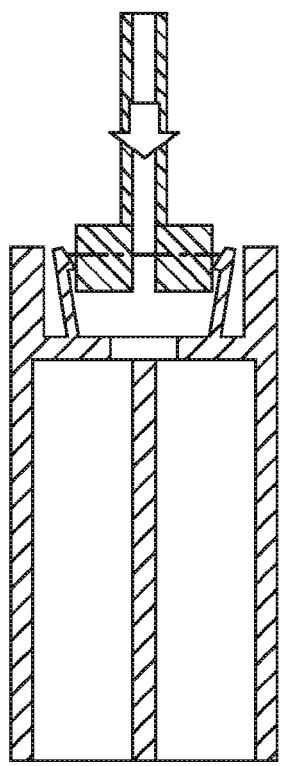
FIGS. 66-68 are cross-sectional side views of a capsule having a snap-fit connection.
Figure 67:
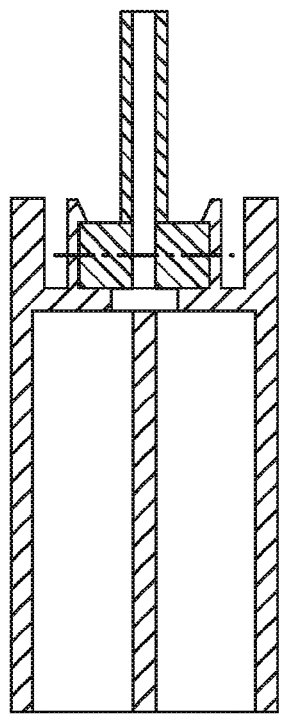
Figure 68:
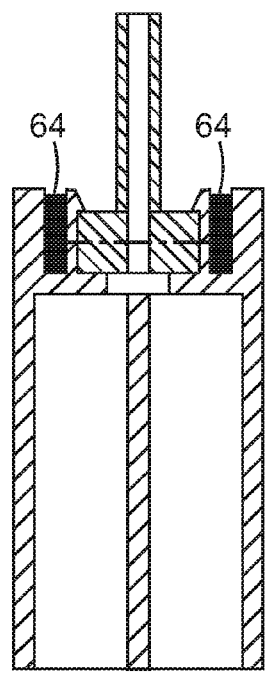

Fitting Cannula with Optional Sealing by Over-Molding (FIG. 66-FIG. 68)

A further possibility for producing the capsule with cannula lies in the formation of a snap-fit connection. The two parts are injected separately and are interlocked in a non-releasable manner by means of a snap-fit connection (FIG. 66 and FIG. 67). It order to ensure a secure fit when the snap-fit connection is loaded, the elastic components can be over-molded (FIG. 68). This can also be done so as to seal the capsule at the same time (not illustrated).

Capsule with Stationary Piston and One-Piece Piston Assembly (FIG. 71-FIG. 74)

The capsules 10 in the embodiments shown in FIG. 71 to FIG. 74 provide a way to store, static mix and directly deliver the mixed material. The piston assembly 54 is one piece with breakable seals 55 between the inner pistons 56 and the outer pistons 57.

Figure 71:
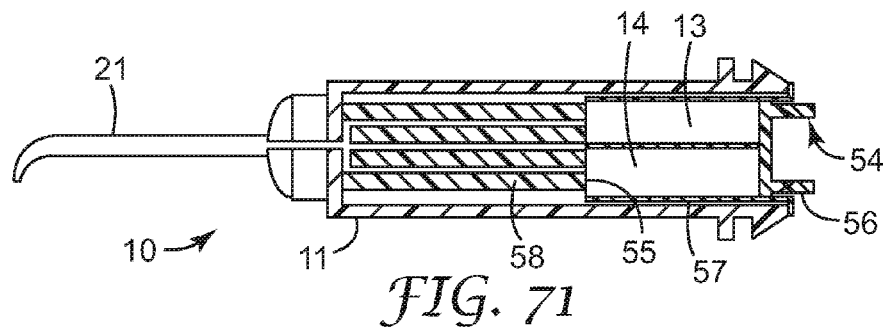
FIGS. 71-74 are cross-sectional side views of a capsule with stationary piston and one-piece piston assembly.
Figure 72:
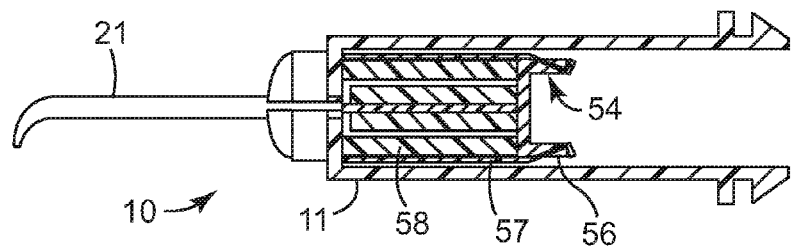

The capsule 10 in the embodiment of FIG. 71 and FIG. 72 is placed in a dispensing gun or applicator 62 (FIG. 69, FIG. 70) and when actuated pushes on the inner piston 56. The capsule seal opens when the seal of the outer piston 57 contacts the stationary capsule piston 58. As the inner piston 56 is pushed in, the pastes are pushed out into the static mixer and mixed for delivery out the tip 21.

Figure 73:
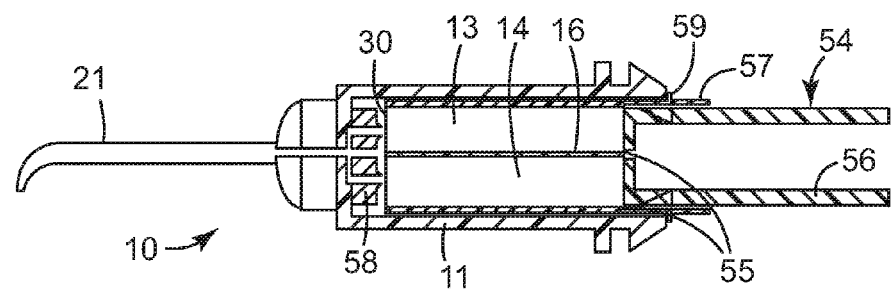
Figure 74:
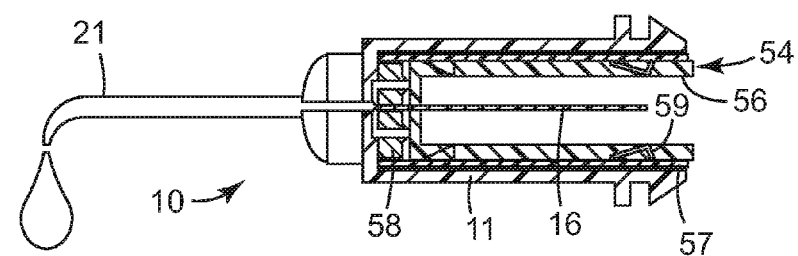

The capsule 10 in the embodiment of FIG. 73 and FIG. 74 is placed in a dispensing gun or applicator 62 (FIG. 69, FIG. 70) and actuated which pushes in the piston assembly 54. The inner piston 56 moves the outer piston 57 in until the seals 30 are opened when it contacts the stationary capsule piston 58. The lock 59 disengages the inner piston 56 from the outer piston 57 when the inner piston 56 travels to the unlocking position. This allows the inner piston 56 to separate from the outer piston 57 by breaking the seal 55 between the two pistons. The inner piston 56 is allowed to continue to travel to push the mixed material out the dispensing tip 21.

All filling methods mentioned may be applied for each of the mentioned capsule configurations. It is as well possible to combine filling methods if it is of advantage.

As foils for sealing the cartridge or to encapsulate the materials in any of the described manner, it is preferred to use multi-layer foils containing at least one aluminum layer. Those foils are well known in the packaging industry. Furthermore it is preferred to use foils with at least one sealing layer as an outer layer of the foil, preferably made out of polyethylene, which provides for a tight seal when the foil is heat-sealed to molded polyethylene parts and/or to the sealing layer of a second foil.

Figure 75:
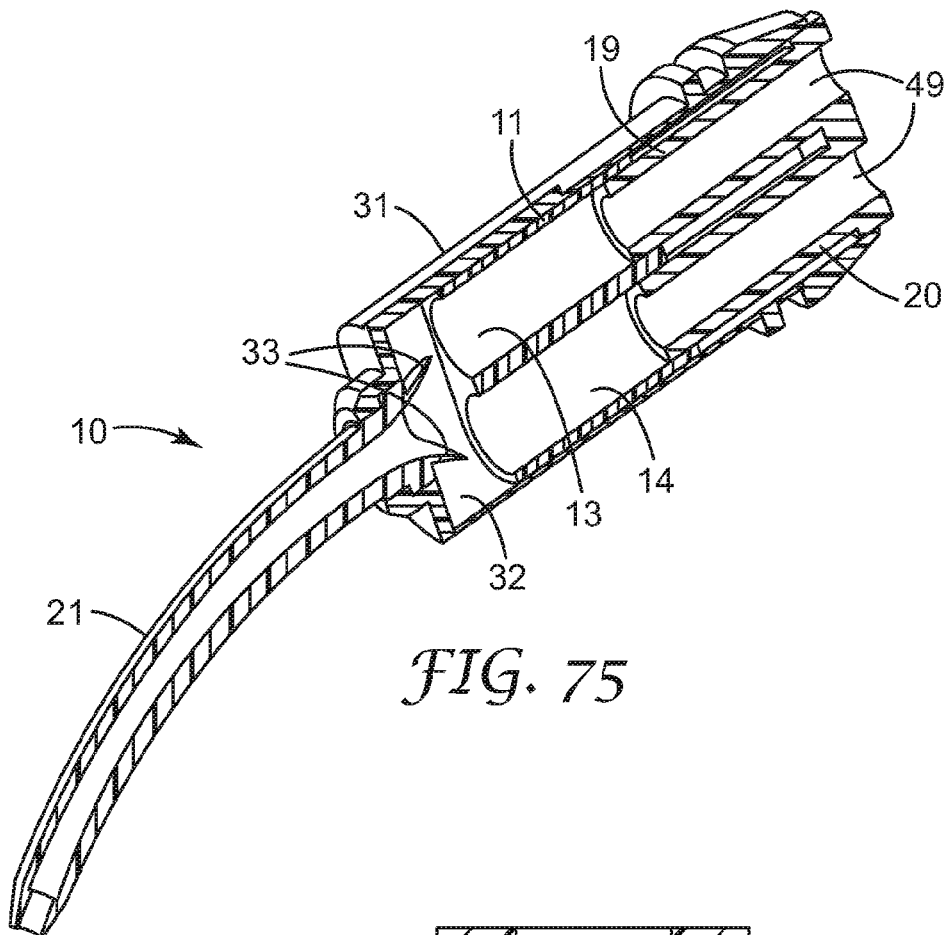
FIG. 75 is an elevated cross-sectional side view of a capsule having piercing elements.

FIG. 75 shows a capsule 10 in a further embodiment similar to the seventh embodiment, and the differences will be described in the following.

The piercing elements 33 for the front foil 30 (not shown) are formed integrally with the cannula 21. The component chambers 13, 14 and the pistons 19, 20 each have circular cross sections. Each piston 19, 20 has a channel 49 extending along its whole length and sits with its front end in the rear portion of the allocated component chamber 13, 14.

A preferred solution for encapsulating the components in the cartridge 11 and to keep them apart from one another is to close the rear end of each component chamber 13, 14 by hotmelt sealing and fitting the pistons 19, 20 into the still soft hotmelt 64 (FIG. 54 to FIG. 56). The front end of each component chamber 13, 14 is closed off by a sealing foil 30 (not shown). When the plunger 63 of an applicator 62 (FIG. 69, FIG. 70) is advanced, the cartridge 11 and the plunger 63 are moved forward because of the hotmelt seal 64 between both parts. When the cartridge 11 has reached the end position in the housing 31, the foil 30 is pierced by the piercing elements or pins 33 which are arranged in the housing 31, and the component chambers 13, 14 are opened. When the plunger 63 is further advanced, the hotmelt seal 64 breaks and the pistons 19, 20 are moved forward thus displacing the material out of the cartridge 11.

Figure 76:
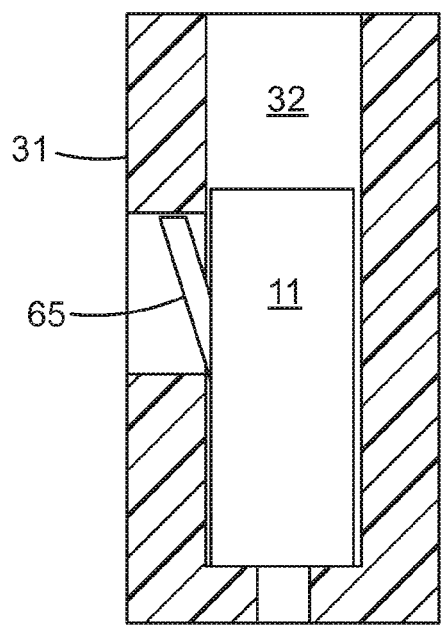
FIG. 76 is a cross-sectional side view of a cartridge affixed by fixing elements.

It may be provided that the cartridge 11 is fixed by fixing elements, preferably by a "snap lock" 65 in the front-end position of the cartridge 11 (FIG. 76). The cartridge 11 is locked as soon it reaches the front-end position in the housing 31.

Alternatively, instead of piercing the foil 30, it may be provided that the foil 30 ruptures because of the pressure of the paste. In this case the cartridge 11 is already mounted in the front-end position in the housing 31. The same snap lock 65 may be used for fixing. When the plunger 63 is advanced, the hotmelt seal 64 breaks and pressurizes the paste which then upon exceeding a certain pressure, forces the foil 30 to rupture.

As hotmelt 64 for all mentioned hotmelt seal solutions preferably polyamide based types like Macromelt 6206 available from Henkel. This type of hotmelt would provide an adhesion break between the hotmelt 64 and the part which is sealed. Sealed parts are preferably made out of polypropylene. Other glue types also those causing a cohesion break (like amorphous alpha-olefines) can also be used.

The invention has now been described with reference to several embodiments thereof. It will be apparent to those skilled in the art that many changes can be made in the embodiments described without departing from the scope of the invention. Thus the scope of the invention should not be limited to the structures described in this application, but only by structures described by the language of the claims and the equivalents of those structures.

LIST OF REFERENCE SIGNS 10 capsule
11 cartridge; 11' front part of 11; 11" rear part of 11
12 outlet of 11, 31; outlet openings of 13, 14
13 first component chamber
14 second component chamber
15 piston
16 partition wall between 13 and 14
17 shells
18 foil on 17
19 first piston
20 second piston
21 cannula
22 mixer
23 rear end of 16
24 first foil
25 second foil
26 stoppers for 12
27 sealing foil on 11
28 sealing foil for rear openings of 13, 14
29 piercing tip
30 sealing foil for front end of 13, 14
31 housing
32 cartridge chamber
33 piercing elements
34 channel through 33
35 connections between 11 and 19, 20
36 membrane between 11 and 19, 20
37 plugs
38 filling nipples
39 through-bore through 37
40 metering or filling needles
41 first component
42 second component
43 stopper
44 overflow volume
45 energy flow directors
46 groove at 11
47 hollow space
48 porous sinter part of 19, 20
49 channels for 64
50 hinge between 11' and 11"
51 hinge between 11' and 21
52 locking elements
53 cap
54 piston assembly
55 seal between 56 and 57
56 inner piston
57 outer piston
58 stationary capsule piston
59 lock between 56 and 57
60 rubber seal
61 connecting piston
62 applicator
63 plunger of 62
64 hotmelt, sealant
65 snap lock
66 air vent channels in 19, 20
67 bulge

What is claimed is:

1. A capsule for two or more components of a material, comprising:
    a cartridge comprising an outlet, a first component chamber for containing a first component, and a second component chamber for containing a second component, the two component chambers opening into the outlet;

a first piston and a second piston, wherein each piston lies with its rear end outside the corresponding component chamber and, when pushed forwards, press the corresponding component out of its component chamber;

the cartridge having an interior with a stepped diameter, the front area being wider than the rear area; and the component chambers being arranged in the front area; wherein the capsule is adapted for use within an applicator having a plunger adapted to advance both pistons to dispense the material.

2. The capsule according to claim 1, wherein the first piston is connected to or formed in one piece with the second piston.

3. The capsule according to claim 1, wherein:

each component chamber is closed off at its rear end by a sealing foil; and each piston lies with its front end behind the outer surface of the allocated sealing foil; and wherein the sealing foil and the allocated piston are configured in such a way that the piston, when advanced into the component chamber, pierces the sealing foil about its entire circumference.

4. The capsule according to claim 1, wherein each component chamber is closed off at its front end by a sealing foil.

5. The capsule according to claim 1, wherein a sealing foil closes off the rear opening of the cartridge.

6. The capsule according to claim 1, wherein a cannula, in which a mixer is arranged, is mounted on the outlet of the cartridge.

7. The capsule according to claim 6, wherein the cannula, in a first position, closes off the outlet of the cartridge and, in a second position, is connected to the outlet of the cartridge.

8. The capsule according to claim 1, wherein the outlet of the cartridge is closed off by a stopper which is connected fixedly to the mixer.

9. The capsule according to claim 1, wherein the centre axis of the capsule and of the cannula is curved.

10. The capsule according to claim 1, wherein the capsule has means which are used for coupling the capsule to an applicator having a single plunger which is advanced when the applicator is actuated.

11. The capsule according to claim 1, wherein the two pistons sit with their rear ends in the cartridge when the piston has not yet been advanced or has been partially or completely advanced.

12. The capsule according to claim 1, wherein at least one of the pistons is connected to or formed in one piece with the cartridge.

13. The capsule according to claim 1, wherein at least one of the component chambers has at least one opening closed by a seal which is a film attached to the cartridge, and wherein the seal is formed in one piece with the cartridge.

14. The capsule according to claim 1, wherein the first component chamber has a rear opening closed by the first piston, wherein:

the first piston has a front end;

the first component chamber has a rear opening for receiving the first piston;

the front end is connected to or formed in one piece with a part of the cartridge surrounding the rear opening and closes the rear opening.

15. The capsule according to claim 1, wherein each component chamber contains the respective component.

16. The capsule according to claim 1, further comprising a cannula pivotably and/or displaceably mounted on the cartridge, which in a first position closes the outlet of the cartridge, and in a second position is connected to the outlet of the cartridge.

* * * * *

UNITED STATES PATENT AND TRADEMARK OFFICE
CERTIFICATE OF CORRECTION

PATENT NO.        : 8,561,845 B2
APPLICATION NO.   : 12/976238
DATED             : October 22, 2013
INVENTOR(S)       : Dean Reidt et al.

It is certified that error appears in the above-identified patent and that said Letters Patent is hereby corrected as shown below:

In the Specification

<u>Column 1</u>

Line 9, delete "U.S." and insert -- U.S.C --, therefor.

<u>Column 12</u>

Line 7, delete "24," and insert -- 24, 25 --, therefor.

<u>Column 21</u>

Line 59, delete "alpha-olefines)" and insert -- alpha-olefins) --, therefor.

Signed and Sealed this
Twenty-fourth Day of June, 2014

Michelle K. Lee
*Deputy Director of the United States Patent and Trademark Office*